United States Patent [19]

Takematsu et al.

[11] Patent Number: 4,468,245
[45] Date of Patent: Aug. 28, 1984

[54] N-(2,3-EPOXYPROPYLENE)-N-ARALKYL-SULFONAMIDE AND HERBICIDAL COMPOSITIONS CONTAINING THE SAME

[75] Inventors: Tetsuo Takematsu; Makoto Konnai; Hiroyoshi Omokawa; Koichi Yoneyama, all of Utsunomiya; Kazuyuki Ushinohama; Seiichi Suzuki, both of Machida, all of Japan

[73] Assignee: Mitsubishi Chemical Industries Ltd., Tokyo, Japan

[21] Appl. No.: 449,989

[22] Filed: Dec. 15, 1982

[30] Foreign Application Priority Data

Dec. 29, 1981 [JP] Japan ................. 56-210922

[51] Int. Cl.$^3$ ............... A01N 43/36; A01N 43/20; C07D 405/12; C07D 303/36
[52] U.S. Cl. ............................ 71/88; 71/95; 549/552; 546/268
[58] Field of Search ............ 549/552; 71/88, 95; 546/268

[56] References Cited

U.S. PATENT DOCUMENTS 4,093,446  6/1978  Bayer et al. .................... 71/88
4,209,318  6/1980  Johnson ........................ 71/88
4,227,009  10/1980 Koch et al. .................... 71/88

FOREIGN PATENT DOCUMENTS 54-46743  4/1979  Japan .
56-55364  5/1981  Japan .

Primary Examiner—Norma S. Milestone
Attorney, Agent, or Firm—Oblon, Fisher, Spivak, McClelland & Maier

[57] ABSTRACT

An N-(2,3-epoxypropylene)-N-aralkylsulfonamide of formula (I):

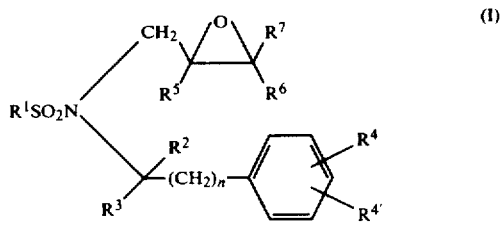

wherein $R^1$ is an alkyl group, a haloalkyl group, an aralkyl group or an aryl group which may be substituted, $R^2$ and $R^3$, independently of each other, are a hydrogen atom or an alkyl group, $R^4$ and $R^{4'}$, independently of each other, are a hydrogen atom, an alkyl group, an alkoxy group or a halogen atom, $R^5$, $R^6$ and $R^7$, independently of each other, are a hydrogen atom, an alkyl group, a haloalkyl group or an aryl group, and n is 0 or 1.

The novel compounds have excellent herbicidal effect based on the physiological selectivity between rice plant and weeds, and have low phytotoxicity against rice plant.

20 Claims, No Drawings

N-(2,3-EPOXYPROPYLENE)-N-ARALKYLSULFONAMIDE AND HERBICIDAL COMPOSITIONS CONTAINING THE SAME

BACKGROUND OF THE INVENTION

1. Field of the Invention

This invention relates to novel compounds, N-(2,3-epoxypropylene)-N-aralkylsulfonamides, having the selective herbicidal activity for waterfield rice plant and also to selective herbicidal compositions comprising the same. More particularly, it relates to N-(2,3-epoxypropylene)-N-aralkylsulfonamides having the physiological selectivity between barnyard grass, which is an annual and a very harmful weed in the paddy field, and the rice plant. In other words, the selective herbicidal activity of the compound is manifested in its ability to fully suppress germination of the barnyard grass without exhibiting any phyto toxicity to waterfield rice plant, and also to selective herbicidal compositions containing the same.

A great number of compounds have been heretofore proposed and put to practice as a herbicide for use in paddy fields. Typical herbicidal compounds which are widely used in paddy field are 2,4,6-trichlorophenyl 4'-nitrophenyl ether (CNP), S-(4-chlorobenzyl) N,N-diethylthiol-carbamate (Benthiocarb), 2-chloro-2',6'-diethyl-N-(butoxymethyl)acetoanilide (Butachlor) and the like. These compounds are not applied based on the physiological selective activity between the barnyard-grass and the waterfield rice plant. The known herbicides for paddy field are applied at the growing stage of rice plant (including transplantation) thereby controlling the germination of barnyard grass. In other words, the difference in chemical resistance of plants which is a function of the differences in the growing stages between barnyard grass and rice plants is utilized for the control of weeds. Another application method is that which makes use of the so-called physical selectivity, which is that because chemicals applied not very deeply to soil are absorbed from the soil by the relatively shallow roots of undesirable plants, the roots of transplanted rice plants, which are relatively deeper, absorb chemicals in only small amounts. For herbicidal application in paddy fields, these two methods are used in most cases.

On the other hand, 3,4-dichloropropionanilide (Propanil) has widely been used in the world because it exhibits selective activity between barnyard grass and rice plant. However, this herbicide is a foliar contact herbicide and has no effect of controlling the germination of barnyard grass. Accordingly, the herbicide should be applied at the growing stage of rice plant similar to CNP and Benthiocarb.

As will be seen from the above, the herbicides for paddy field which are currently employed are not those which are based on the physiological selectivity at the time of germination of barnyard grass and rice plants. The herbicides of the just-mentioned type are very difficult to apply especially in fields transplanted with young seedlings or in fields undergoing direct sowing cultivation where the cultivation area has drastically increased as a result of the recent introduction of machines, because the waterfield rice seedlings are weak and, as a consequence, may readily suffer phytotoxicity. Accordingly, there is the strong demand for the development of compounds which exhibit harmless herbicidal activity in such fields or which exhibit pysiological selective activity between the barnyardgrass and the rice plant.

Compounds which exhibit physiological selective activity between the barnyardgrass and the rice plant have been proposed, for example, in Japanese patent application No. 52-114034 and are N-substituted benzyl-benzenesulfonamides represented by formula (i);

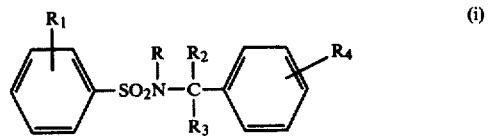

wherein $R_1$ represents a substituent selected from the group consisting of a hydrogen atom, a lower alkyl group, a lower alkoxy group and a halogen atom, $R_2$ and $R_3$ represent a substituent selected from the group consisting of a hydrogen atom and a methyl group, but $R_2$ and $R_3$ in the same molecule both are not hydrogen atoms, $R_4$ represents a substituent selected from the group consisting of a hydrogen atom, a methyl group, a methoxy group and a halogen atom, and R represents an alkyl group or an alkenyl group which may have a dimethylamino group, a cyano group, a methoxy group or an ethynyl group. The reference also shows selective herbicides comprising compound (i) as an effective component or ingredient. However, these compounds have the drawback that they exhibit herbicidal activity unsatisfactory and they are limited in the kinds of weeds which they are able to kill.

Japanese patent application No. 54-130982, discloses N-allyl-N-benzylbenzenesulfonamides represented by formula (ii) and selective herbicides comprising an effective amount of the compound:

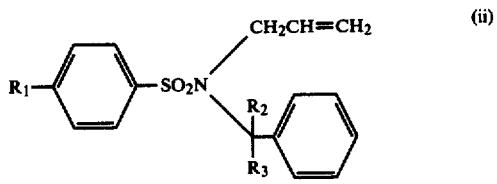

wherein $R_1$ represents a substituent selected from the group consisting of a hydroxy group, an amino group, a lower alkenyloxy group, a benzoyloxy group with or without being substituted with a halogen atom, a lower alkyloxymethoxy group, a halogenated lower alkyloxy group, an alkylureido group, a methanesulfonylamide group, fatty acid amido with or without being substituted with a halogen atom, a methanesulfonyloxy group, an alkylcarbamoyloxy group and a tolylcarbamoyloxy group, and $R_2$ and $R_3$ each represents a substituent selected from the group consisting of a hydrogen atom and a methyl group provided that both the substituents are not hydrogen at the same time.

However, these compounds also exhibit an unsatisfactory herbicidal activity, coupled with the fact that they are toxic to fish. They are thus unfavorable as a herbicide.

Intensive studies have been made on compounds which exhibit substantial physiological selective activity between the barnyardgrass and the waterfield rice plant and the present compounds being N-(2,3-epoxypropylene)-N-aralkylsulfonamides are the result of this study.

SUMMARY OF THE INVENTION

According to the present invention, there is provided an N-(2,3-epoxypropylene)-N-aralkylsulfonamide represented by the following formula (I)

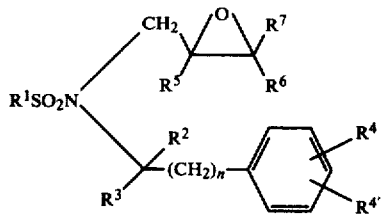

in which $R^1$ represents an alkyl group, a haloalkyl group, an aralkyl group or an aryl group which may have substituents, $R^2$ and $R^3$ may be the same or different and represent a hydrogen atom or an alkyl group, $R^4$ and $R^{4'}$ may be the same or different and represent a hydrogen atom, an alkyl group, an alkoxy group or a halogen atom, $R^5$, $R^6$, and $R^7$ may be the same or different and represent a hydrogen atom, an alkyl group, a haloalkyl group or an aryl group, and n is a value of 0 or 1. Also provided are selective herbicides comprising the amide compounds as an effective component and a process for preparing the compounds.

DETAILED DESCRIPTION OF THE PREFERRED EMBODIMENTS

In the N-(2,3-epoxypropylene)-N-aralkylsulfonamides of the present invention of formula (I) (hereinafter referred to simply as amide compound), $R^1$ is an alkyl group having from 1 to 4 carbon atoms, a haloalkyl group having a chlorine, bromine, fluorine or iodine substituent and from 1 to 4 carbon atoms, an aralkyl group such as benzyl, phenethyl or the like, or a substituted or unsubstituted aryl group such as a 5,6,7,8-tetrahydro-2-naphthyl group; a 2-indanyl group and a group represented by the formula,

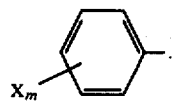

In the just-mentioned formula, X represents an alkyl group; a cycloalkyl group; a halogen atom; a nitro group; an amino group; an alkylcarbonyl group; a hydroxy group; an alkoxy group; a haloalkoxy group; an alkenyloxy group; an aralkyloxy group; an alkoxyalkoxy group; an alkylcarbamoyloxy group; an alkylcarbamoyl group; a N-alkyl-N-phenylcarbamoyloxy group; an alkylsulfonyloxy group; a phenoxy, benzyloxy or pyridyloxy group which may be substituted with an alkyl group, a halogen atom or a nitro group; an alkoxycarbonyloxy group; an alkoxycarbonylalkoxy group; an alkylsulfamoyloxy group; a benzoyloxy group; an epoxyalkoxy group; an alkylcarbonyloxy group; an alkoxycarbonylamino group; a di-substituted carbamoylamino group; or an alkoxycarbonylalkylamino group. The symbol m is an integer of from 0 to 5.

When $m \geq 2$, the substituents X may be the same or different.

$R^2$ and $R^3$ may be the same or different and each represents a hydrogen atom or an alkyl group having from 1 to 5 carbon atoms. $R^4$ and $R^{4'}$, independently from each other, are a hydrogen atom, a halogen atom selected from chlorine, bromine, fluorine and iodine, or an alkyl or alkoxy group having from 1 to 3 carbon atoms.

$R^5$, $R^6$, and $R^7$ may be the same or different and each represents a hydrogen atom, an alkyl group having from 1 to 3 carbon atoms, a haloalkyl group having a substituent of chlorine, bromine, fluorine or iodine, or an aryl group such as benzene.

In the above definition, the alkyl group may be either a linear or branched alkyl group.

Judging from the herbicidal activity, preferable compounds are those of the formula (I) in which $R^1$ is a 5,6,7,8-tetrahydro-2-naphthyl group, 2-indanyl group or a group which is represented by the formula,

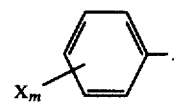

In the just-mentioned formula, X is an alkyl group having from 1 to 5 carbon atoms; a cycloalkyl group; a halogen atom; an amino group; a hydroxy group; an alkoxy group; a haloalkoxy group; an alkenyloxy group; an aralkyloxy group; an alkoxyalkoxy group; an alkylcarbamoyloxy group; an alkylcarbamoyl group; a N-alkyl-N-phenylcarbamoyloxy group; an alkylsulfonyloxy group; a phenoxy, benzyloxy or pyridyloxy group with or without being substituted with an alkyl group, a halogen atom or a nitro group; an alkoxycarbonyloxy group; an alkoxycarbonylalkoxy group; an alkylsulfamoyloxy group; a benzoyloxy group; an epoxy alkoxy group; an alkylcarbonyloxy group; an alkoxycarbonylamino group; a N-alkyl-N-alkoxycarbamoylamino group; or an alkoxycarbonylalkylamino group.

In the formula (I), at least one of $R^2$ and $R^3$ is preferably an alkyl group having from 1 to 3 carbon atoms. $R^4$ and $R^{4'}$ are preferably a hydrogen atom, or an alkyl group or an alkoxy group having from 1 to 3 carbon atoms. $R^5$, $R^6$ and $R^7$ are preferably a hydrogen atom. Preferably n is 0.

More preferably, at least one of $R^2$ and $R^3$ is a methyl group.

Most preferable compounds are compounds of formula (I), wherein $R^1$ is a 5,6,7,8-tetrahydro-2-naphthyl group; $R^1$ is a

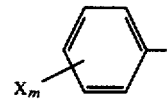

group and X is an alkyl group, m is an integer of from 0 to 4, and $R^3$, $R^4$ and $R^{4'}$ is a hydrogen atom; X is an alkyl group or an alkoxy group, m is an integer of 0 or 1, $R^4$ is a methoxy group located at the 3-position of the benzene ring to which it is bonded, and $R^3$ and $R^{4'}$ are each a hydrogen atom; X is an alkyl group, m is an integer of from 0 to 2, $R^2$ and $R^3$ are each an alkyl group, one of $R^2$ and $R^3$ is a methyl group and the other is an alkyl group, and $R^4$ and $R^{4'}$ are each a hydrogen atom; and X is a dialkylcarbamoyl group or a dialkylcarbamoyloxy group wherein an alkyl group has 1 or 2 carbon atoms, $R^2$ is a methyl group, and $R^3$, $R^4$ and $R^{4'}$ are each a hydrogen atom.

It should be noted that when $R^2$ and $R^3$ in the afore-indicated formula (I) are different from each other, diastereomers are present and generally the compound obtained is a mixture of these diastereomers. These diastereomers both exhibit the herbicidal activity.

The amide compounds of the present invention can be prepared, for example, by the following procedures.

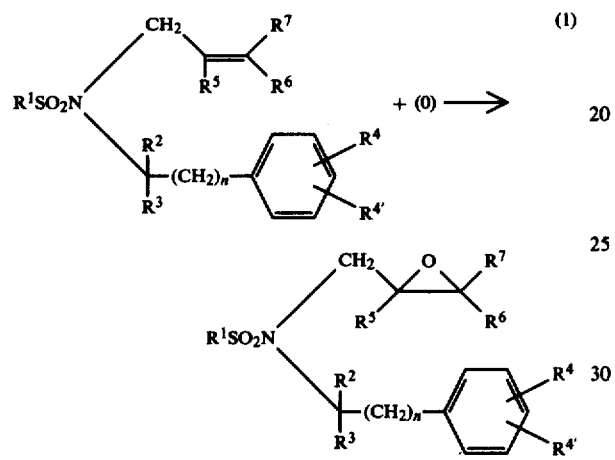

The symbols $R^1$, $R^2$, $R^3$, $R^4$, $R^{4'}$, $R^5$, $R^6$, $R^7$ and n have the same meanings, as defined before.

The above reaction is conveniently effected in solvents. Suitable solvents are chloroform, dichloromethane, carbon tetrachloride and the like. The oxidizing agent is preferably metachloroperbenzoic acid. The reaction temperature is a temperature at which the solvent is refluxed and the reaction time ranges from 1 to 5 hours.

The starting material of the formula (II) is prepared according to the following procedure.

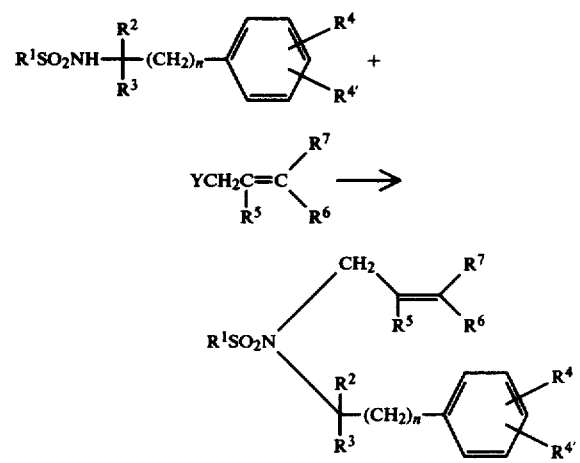

in which $R^1$, $R^2$, $R^3$, $R^4$, $R^{4'}$, $R^5$, $R^6$, $R^7$ and n have the same meanings as defined before, and Y represents a halogen atom.

The reaction is favorably conducted in solvents. Any solvent may be used for this purpose insofar it does not take part in the reaction. Suitable solvents include ethers such as diethyl ether, dioxane, tetrahydrofuran and the like; aromatic hydrocarbons such as benzene, toluene, xylene and the like; N,N-dimethylformamide; dimethylsulfoxide; water; pyridine; and the like.

The reaction is carried out in the presence of a catalyst. Examples of the catalyst include alkali metal hydroxides such as sodium hydroxide, potassium hydroxide and the like; metallic sodium; metal hydrides such as sodium hydride, potassium hydride and the like; and organic bases such as pyridine, triethylamine and the like. Especially, sodium hydroxide and potassium hydroxide are preferably used in combination with water as solvent, and sodium hydride is preferably used when aromatic hydrocarbons, N,N-dimethylformamide and dimethylsulfoxide are used as solvent. The reaction temperature is in the range of room temperature to a refluxing temperature for the solvent and the reaction time may vary depending on the reaction temperature and the type of the reagent used and is usually in the range of 1 to 10 hours.

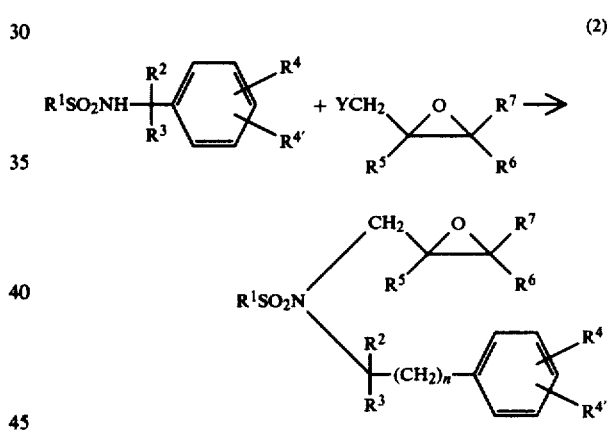

The symbols $R^1$, $R^2$, $R^3$, $R^4$, $R^{4'}$, $R^5$, $R^6$, $R^7$, n and Y have the same meanings as defined before.

Among the compounds of the present invention, those of the afore-indicated formula in which X is a nitro group or an alkyl group can favorably be obtained according to the above reaction.

This reaction is conveniently effected in solvents. Examples of the solvents include ethers such as diethyl ether, tetrahydrofuran and the like; N,N-dimethylformamide; dimethylsulfoxide; epichlorohydrin; and the like.

The reaction is carried out in the presence of a catalyst. Preferable examples of the catalyst include metal hydrides such as sodium hydride, potassium hydride and the like. The reaction temperature is in the range of room temperature to a temperature at which the solvent is refluxed. The reaction time may vary depending on the reaction temperature and the type of the reagent used and is usually in the range of 1 to 10 hours.

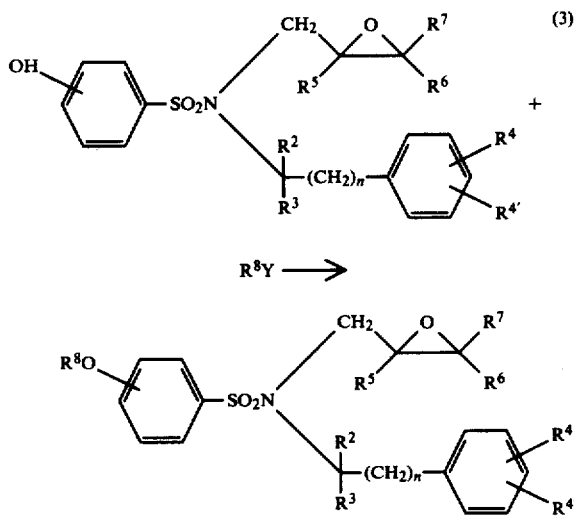

The symbols $R^1$, $R^2$, $R^3$, $R^4$, $R^{4'}$, $R^5$, $R^6$, $R^7$, n and Y have the same meanings as defined before, and $R^8$ represents an alkylcarbonyl group, a haloalkyl group, an aryl group which may be substituted, an alkylcarbamoyl group, a phenylcarbamoyl group, an alkoxycarbonyl group, an alkylsulfamoyl group, an alkylsulfonyl group or a benzyl group which may be substituted.

By the above reaction, those compounds of the formula where X is an alkylcarbonyloxy group, a haloalkoxy group, an aryloxy group which may be substituted, an alkylcarbamoyloxy group, a phenylcarbamoyloxy group, an alkoxycarbonyloxy group, an alkylsulfamoyloxy group, an alkylsulfonyloxy group, or a benzyloxy group which may be substituted are suitably obtained.

The reaction is favorably effected in solvents. Examples of the solvents include water; ketones such as acetone, methyl ethyl ketone, methyl isobutyl ketone and the like; N,N-dimethylformamide; pyridine; dimethylsulfoxide; and the like. Ketones are most preferable. The reaction is carried out in the presence of a dehydrohalogenation agent and a catalyst. The dehydrohalogenation agents include, for example, alkali metal hydroxides such as sodium hydroxide, potassium hydroxide and the like, potassium carbonate, triethylamine, pyridine and the like.

The catalyst is preferably potassium iodide. The reaction temperature ranges from room temperature to a refluxing temperature for solvent. The reaction time depends on the reaction temperature and the type of the reagent and is usually in the range of 1 to 10 hours.

Moreover, N-(2,3-epoxypropylene)-N-aralkylsulfonamide of the formula (I), wherein X is an amino group, can be prepared by reducing the corresponding compound of the formula (I) wherein X is a nitro group.

Also, each compound of the formula (I), wherein X is an alkylcarbonylamino group, an alkoxycarbonylamino group, a di-substituted carbamoylamino group or an alkoxycarbonylalkylamino group, can be prepared by reacting the corresponding compound of the formula (I) wherein X is an amino group with an acyl halide, an alkyl haloformate, a di-substituted carbamoyl halide or an alkylhaloalkanoate.

The compounds of the present invention exhibit the substantial physiological selective activity between the barnyardgrass and the rice plant, with the advantage that they can be applied at all the growing stages of the rice plant ranging from the stage of germination until the growing stage. Especially, these compounds have the prominent feature that they are quite innocuous when applied to rice plants which are directly sown in a submerged condition, which mode of application cannot be used for known herbicides. Accordingly, the compounds of the present invention can be admixed with rice seeds and applied simultaneously, so that the labor for applying a herbicide can fully be saved.

The physiological selective activity of the compounds of the invention is more particularly described. As is shown in Experimental Example 3 appearing hereinafter, when seeds of barnyardgrass and rice plant are simultaneously applied to a paddy field to which is applied Compound No. 102 or 104 of Table 1 in an amount of 12.5 g/are, the barnyardgrass is completely prevented from growing. However, it is found that even when the same compound as mentioned above is applied in an amount of 100 g, the rice plant suffers no adverse influence and grows normally in a manner similar to a nontreated plot. This reveals that even when the compounds of the invention are used in an amount of about 8 times by weight the amount sufficient to completely control the growth of barnyard grass the growth of rice plant is not damaged. From this it can be seen that the compounds of the invention exhibit physiologically, very high selective activity.

Although the compounds of the invention vary in the physiological activity depending on the type and position of modifying functional groups, they have the common characteristic that they produce only very small phytotoxicity against waterfield rice plant. The compounds of the invention exhibit the highest weed-killing spectrum against barnyardgrass and high sensitivity against tooth cup (*Rotala indica*), ducktongue weed (*Monochroia vaginalis*), smallflower umbrellaplant (*Cyperus difformis*), hardstem bulrush (*Scirpus juncoides*) and the like.

Although the compounds of the invention show relatively low activity against mature grown wide-leaf weeds and slender spikerush (*Eleocharis acicularis*), use of herbicides which are effective against these weeds, e.g. 2-methyl-4-chlorophenoxybutyric acid (MCPB), N-phenyl(β-naphthoxy)acetamide (MT-101) and the like, in admixture with the compounds of the invention will enlarge the width of the weed-killing spectrum.

The amide compounds may be used as a herbicide without use of any auxiliary agents and are usually applied in the form of a wettable powder, emulsion, granular or dust which is prepared according to the usual technique for producing herbicides using suitable inactive liquid or solid carriers and surfactants.

Examples of the liquid carriers include toluene, xylene, methylnaphthalene, cyclohexane, butanol, glycol, dimethylsulfoxide, dimethylformamide, acetone, methyl isobutyl ketone, animal and plant oils, fatty acids, fatty acid esters, water and the like.

Examples of the solid carriers include clay, kaolin, talc, bentonite, diatomaceous earth, silica, calcium carbonate, plant flours such as soybean flour and wheat bran, and the like.

As a matter of course, the herbicides comprising the compounds of the invention may be applied in admixture with other known agricultural chemicals such as, for example, insecticides, bacteriocides, other herbicides, growth controllers and fertilizers.

The herbicidal composition according to the invention has preferably the following proportions of the active ingredient and auxiliary agents.

|  | Active Ingredient | Surfactant | Carrier | (% by weight) Other Additive |
|---|---|---|---|---|
| Wettable powder | 5 to 80 | 2 to 20 | 10 to 93 | 0 to 5 |
| Granular | 1 to 20 | 2 to 10 | 70 to 97 | 0 to 5 |
| Emulsion | 5 to 80 | 5 to 30 | 10 to 90 | 0 to 5 |
| Dust | 2 to 10 | 0 to 5 | 85 to 98 | 0 to 5 |

The amide compounds of the invention are conveniently used for the soil treatment in the submerged paddy field and also in the upland field at the time prior to germination of weeds till the germination. The amount of the effective ingredient is in the range of from 5 to 100 g/are, preferably 10 to 25 g/are.

The present invention is illustrated by way of the following Synthetic Examples, Preparatory Examples and Herbicidal Experimental Examples, which should not be construed as limiting the invention.

Synthetic Example 1

N-(2,3-epoxypropyl)-N-α-methylbenzyl-4-propylbenzenesulfonamide

A solution of 3.27 g (0.01 mole) of N-allyl-N-α-methylbenzyl-4-propylbenzenesulfonamide in 30 ml of chloroform was admixed with 4.31 g (0.02 mole) of meta-chloroperbenzoic acid for reaction under reflux for 2 hours. Thereafter, an aqueous sodium sulfite solution was added to decompose the excess of the peroxide. After washing with an aqueous sodium bicarbonate solution and water, the chloroform solution was dried over anhydrous magnesium sulfate, concentrated and purified by the silica gel chromatography to obtain the intended product (Compound No. 14). The yield was 91% and the $n_D^{25.0}$ value was found to be 1.5445. The elemental analysis of the product was effected with the results shown below.

| Results of Elemental Analysis ($C_{20}H_{25}N_1O_3S_1$) | | | | |
|---|---|---|---|---|
|  | C | H | N | S |
| Calculated | 66.82 | 7.01 | 3.90 | 8.90 |
| Found | 66.80 | 7.03 | 3.87 | 8.87 |

In the similar manner as in Synthetic Example 1, there were obtained Compound Nos. 1~6, 12, 13, 15, 22~28, 36, 80~132, 135~138, 151~157, 167~170, 172~178, 180~186, 188~196, 198~201, 203~208 and 210~212 of Table 1. The chemical structures of these compounds were, respectively, confirmed by the I.R. spectrum and N.M.R. spectrum analyses.

Synthetic Example 2

N-(2,3-epoxypropyl)-N-α-methylbenzyl-2-nitrobenzenesulfonamide 2.1 g (6.6 mmol) of N-α-methylbenzyl-2-nitrobenzenesulfonamide was dissolved in 10 ml of epichlorohydrin, to which was gradually added at room temperature 0.35 g (7.3 mmol) of 50% sodium hydride, followed by agitating at room temperature for 30 minutes and reacting under reflux for 1 hour. The epichlorohydrin was distilled off under reduced pressure, water was added and extracted with ethyl acetate. The ethyl acetate phase was dried over anhydrous magnesium sulfate, concentrated, and purified by the silica gel chromatography to obtain the intended product (Compound No. 33). The yield was 97% and the $n_D^{26.5}$ value was 1.5572. The results of the elemental analysis are shown below.

| Results of Elemental Analysis ($C_{17}H_{18}N_2O_5S_1$) | | | | |
|---|---|---|---|---|
|  | C | H | N | S |
| Calculated | 56.34 | 5.01 | 7.73 | 8.83 |
| Found | 56.30 | 4.97 | 7.75 | 8.80 |

In the similar manner as in Synthetic Example 2, there were obtained Compound Nos. 9, 16, 19, 34 and 35 of Table 1. The chemical structures of these compounds were confirmed by the I.R. and N.M.R. analyses.

Synthetic Example 3

N-(2,3-epoxypropyl)-α-methylbenzyl-4-(N,N-dimethylcarbamoyloxy)benzenesulfonamide 1 g (3 mmol) of N-(2,3-epoxypropyl)-N-α-methylbenzyl-4-hydroxybenzenesulfonamide and 180 mg (3.75 mmol) of 50% sodium hydride were added to 15 ml of dry N,N-dimethylformamide, followed by agitating at room temperature for 30 minutes. To the resulting sodium salt was added 400 mg (3.83 mmol) of N,N-dimethylcarbamoyl chloride for reaction at 60° C. for 1 hour. After completion of the reaction, the excess of the solvent and N,N-dimethylcarbamoyl chloride were removed by distillation under reduced pressure. The residue was dissolved in chloroform and sufficiently washed with water and the chloroform solution was dehydrated over anhydrous magnesium sulfate, followed by distilling off the solvent to obtain a crude product. The crude product was purified by the silica gel chromatography to obtain 980 mg of N-(2,3-epoxypropyl)-N-α-methylbenzyl-4-(N,N-dimethylcarbamoyloxy)-benzenesulfonamide (Compound No. 57). The $n_D^{26.0}$ value was found to be 1.5320. The results of the elemental analysis are shown below.

| Results of Elemental Analysis ($C_{20}H_{24}N_2O_5S_1$) | | | | |
|---|---|---|---|---|
|  | C | H | N | S |
| Calculated | 59.40 | 5.98 | 6.93 | 7.92 |
| Found | 59.37 | 6.01 | 6.93 | 7.89 |

In the similar manner as in Synthetic Example 3, Compound Nos. 51~56, 58, 60~65, 76 and 158~162 were obtained. The structures of these compounds were confirmed by the I.R. and N.M.R. analyses.

Synthetic Example 4

N-(2,3-epoxypropyl)-N-α-methylbenzyl-4-methoxybenzenesulfonamide 552 mg (0.012 mol) of 50% sodium hydride was gradually added to 29.1 g (0.01 mol) of N-α-methylbenzyl-4-methoxybenzenesulfonamide obtained by reaction between 4-methoxybenzenesulfonyl chloride and α-methylbenzylamine and 9.25 g (0.1 mol) of epichlorohydrin, followed by refluxing for 2 hours.

After completion of the reaction, the excess epichlorohydrin was distilled off under reduced pressure and the residue was dissolved in chloroform and washed sufficiently with water. The chloroform solution was dried over anhydrous magnesium sulfate, followed by distilling off the solvent to obtain a crude product. The crude product was purified by the silica gel chromatography to obtain 3.16 g of N-(2,3-epoxypropyl)-N-α-methylbenzyl-4-methoxybenzenesulfonamide (Compound No. 38). This compound had a mleting point of 68.0° to 72° C. The results of the elemental analysis are shown below.

| Results of Elemental Analysis ($C_{18}H_{21}N_1O_4S_1$) | | | | |
| --- | --- | --- | --- | --- |
| | C | H | N | S |
| Calculated | 62.23 | 6.09 | 4.03 | 9.23 |
| Found | 62.20 | 6.11 | 3.99 | 9.22 |

In the similar manner as in Synthetic Example 4, there were also obtained Compound Nos. 39~50, 59, 66~74, 77~79, 171, 179, 187, 197, 202 and 209. The chemical structures of these compounds were confirmed by the I.R. and N.M.R. analyses.

Synthetic Example 5

N-(2,3-epoxypropyl)-N-α-methylbenzyl-4-hydroxybenzenesulfonamide

To a solution of 1.61 g (0.01 mol) of N-allyl-N-α-methylbenzylamine and 1.38 g of potassium carbonate in 15 ml of acetone was dropped a solution of 2.62 g (0.084 mol) of 4-benzoyloxybenzenesulfonyl chloride in 5 ml of acetone under ice-cooling conditions. The mixture was subjected to the reaction at room temperature for 30 minutes and then at 50° C. for 1 hour. After completion of the reaction, the inorganic salt was removed by filtration and the acetone was distilled off, then, the contents were admixed with 150 ml of a 20% potassium hydroxide solution in ethanol, followed by refluxing for 30 minutes. After completion of the reaction, the reaction mixture was poured into ice-water to permit crystals to precipitate. The crystals were washed with a dilute acidic solution and a dilute alkaline solution, followed by sufficiently washing with water, drying in vacuum and recrystallizing from a mixed solvent of benzene and n-hexane to obtain 2.00 g of N-allyl-N-α-methylbenzyl-4-hydroxybenzenesulfonamide (melting point 128° to 129° C.).

5 ml of chloroform solution containing 1 g (3.2 mmol) of N-allyl-N-α-methylbenzyl-4-hydroxybenzenesulfonamide was added to 30 ml of a chloroform solution of 828 mg (4.8 mmol) of metachloroperbenzoic acid, followed by refluxing for 2 hours. After completion of the reaction, the chloroform solution was washed with an aqueous sodium thiosulfate solution and then an aqueous sodium bicarbonate solution. After drying, the solvent was distilled off and the resulting crude product was purified by the silica gel column chromatography (hexane-ethyl acetate) to obtain 910 mg of N-(2,3-epoxypropyl)-N-α-methylbenzyl-4-hydroxybenzenesulfonamide (Compound No. 37). The melting point was found to be 82.0° to 86.0° C. The results of the elemental analysis are shown below.

| Results of Elemental Analysis ($C_{17}H_{19}N_1O_4S_1$) | | | | |
| --- | --- | --- | --- | --- |
| | C | H | N | S |
| Calculated | 61.24 | 5.74 | 4.20 | 9.62 |
| Found | 61.25 | 5.71 | 4.19 | 9.59 |

In the similar manner as in Synthetic Example 5, there was also obtained Compound No. 75 of Table 1. The chemical structure of this compound was confirmed by the I.R. and N.M.R. analyses.

Synthetic Example 6

Synthesis of N-(2,3-epoxypropylene)-N-(α-methylbenzyl)-2-toluenesulfonamide and Separation of the produced diastereomer 15.6 g (0.05 mol) of N-allyl-N-(α-methylbenzyl)-2-toluenesulfonamide and 21.5 g (0.10 mol) of 80% metachloroperbenzoic acid were dissolved in 150 ml of chloroform and reacted under reflux for 2 hours. After completion of the reaction, an aqueous sodium sulfite solution was added to decompose the excess of the peroxide. The reaction mixture was washed with an aqueous sodium bicarbonate solution and water and the chloroform solution was dried over anhydrous magnesium sulfate. The silica gel thin layer chromatography (solvent for development: ethyl acetate:n-hexane 1:4) of the resulting product revealed formation of two products at Rf values of 0.28 and 0.22, respectively. After removal of the solvent by distillation, the residue was separated by the silica gel chromatography (developing solvent: ethyl acetate:n-hexane=1:4) to obtain 6.3 g of Compound No. 7 (having a higher Rf value) and 7.2 g of Compound No. 8 (having a lower Rf value) indicated in Table 1.

In the similar manner as described above, there were also obtained combinations of Compound No. 10 (having a higher Rf value) and Compound No. 11 (having a lower Rf value), Compound No. 17 (having a higher Rf value) and Compound No. 18 (having a lower Rf value), Compound No. 20 (having a higher Rf value) and Compound No. 21 (having a lower Rf value), Compound Nos. 29 (having a higher Rf value) and 30 (having a lower Rf value), Compound Nos. 31 (having a higher Rf value) and 32 (having a lower Rf value), and Compound Nos. 133 (having a higher Rf value) and 134 (having a lower Rf value). Their chemical structures were confirmed by the elementary, I.R. and N.M.R. analyses.

Synthetic Example 7

N-(2,3-epoxypropylene)-N-(α-methyl benzyl)-4-aminobenzenesulfonamide 5.2 g of iron powder was added to the mixture of 0.5 g of acetic acid and 3.5 g of water, followed by agitating at refluxed temperature for 30 minutes. The reaction mixture was cooled to 80° C. 5.0 g of N-(2,3-epoxypropylene)-N-(α-methylbenzyl)-4-nitrobenzenesulfonamide suspended in 9 ml of isopropylalcohol was added to the reaction mixture, followed by vigorous agitation at 80° C. for 1 hour.

After cooling, acetone was added to the reaction mixture, and the solution was filtered. Ethylacetate was added to the filtrate, then the ethylacetate solution was washed with a dilute alkaline solution, dried over anhydrous magnesium sulfate, concentrated to obtain the intended product (Compound No. 139). The yield was 90% and the m.p. was 120.0° C. to 121.0° C. The elemental analysis of the product was effected with the results shown below.

| Results of Elemental Analysis ($C_{17}H_{20}N_2O_3S_1$) | | | | |
|---|---|---|---|---|
| | C | H | N | S |
| Calculated | 61.42 | 6.06 | 8.43 | 9.64 |
| Found | 61.38 | 5.98 | 8.47 | 9.68 |

In the similar manner as in Synthetic Example 7, there were obtained Compound No. 144 and 149 of Table 1. The chemical structures of these compounds were, respectively, confirmed by the I.R. spectrum and N.M.R. spectrum analysis.

Synthetic Example 8

N-(2,3-epoxypropylene)-N-(α-methylbenzyl)-3-methoxycarbonylaminobenzenesulfonamide 0.53 g of methylchloroformate was added dropwise to a ethylacetate solution of 1.7 g of N-(2,3-epoxypropylene)-N-(α-methybenzyl)-3-aminobenzenesulfonamide and 0.62 g of triethylamine under ice cooling condition. After completion of dropping, the mixture was stirred for 2 hours. The organic layer was washed with water, dried over anhydrous magnesium sulfate, concentrated and purified by the silica gel chromatography to obtain 1.5 g of N-(2,3-epoxypropylene)-N-(α-methylbenzyl)-3-methoxycarbonylbenzenesulfonamide (Compound No. 146). The yield was 77% and the $n_D^{24.5}$ value was found to be 1.5458. The elemental analysis of the product was effected with the results shown below.

| Results of Elemental Analysis ($C_{19}H_{22}N_2O_5S_1$) | | | | |
|---|---|---|---|---|
| | C | H | N | S |
| Calculated | 58.45 | 5.68 | 7.17 | 8.21 |
| Found | 58.50 | 5.65 | 7.15 | 8.18 |

In the similar manner as in Synthetic Example 8, there were obtained Compound No. 140~142, 145~147 and 150 of Table 1. The chemical structures of these compounds were, respectively, confirmed by the I.R. spectrum and N.M.R. spectrum analysis.

Synthetic Example 9

N-(2,3-epoxypropylene)-N-(α-methylbenzyl)-3-(1-ethoxycarbonylethylamino)benzenesulfonamide 1.7 g of N-(2,3-epoxypropylene)-N-(α-methylbenzyl)-3-aminobenzene was reacted with 2.3 g of ethyl-α-bromopropionate in the presence of 1.1 g of potassium carbonate for 3 hours. After cooling, ethyl acetate was added to the reaction mixture, and the ethyl acetate solution was washed with water, dried over anhydrous magnesium sulfate, concentrated and purified by the silica gel chromatography to obtain 1.8 g of N-(2,3-epoxypropylene)-N-(α-methylbenzyl)-3-(1-ethoxycarbonylethylamino)benzenesulfonamide (Compound No. 148). The yield was 83% and the $n_D^{24.5}$ value was found to be 1.5521. The elemental analysis of the product was effected with the results shown below.

| Results of Elemental Analysis ($C_{22}H_{28}N_2O_5S_1$) | | | | |
|---|---|---|---|---|
| | C | H | N | S |
| Calculated | 61.09 | 6.53 | 6.48 | 7.41 |
| Found | 61.07 | 6.55 | 6.52 | 7.31 |

In the similar manner as in Synthetic Example 9, there was obtained Compound No. 143 of Table 1. The chemical structures of these compounds were, respectively, confirmed by the I.R. spectrum and N.M.R. spectrum analysis.

Synthetic Example 10

N-(2,3-epoxypropylene)-N-(α-methylbenzyl)-4-(N,N-dimethylcarbamoly)benzenesulfonamide 5.4 g of metachlorperbenzoic acid was added to a chloroform solution of 3.7 g of N-allyl-N-(α-methylbenzyl)-4-(N,N-dimethylcarbamoyl)benzenesulfonamide obtained by reaction between dimethylamine and N-allyl-N-(α-methylbenzyl)-4-chlorocarbonylbenzenesulfonamide. The mixture was reacted under reflux for 2 hours. Thereafter, an aqueous sodium sulfite solution was added to decompose the excess of the peroxide. After washing with an aqueous sodium bicarbonate solution and water, the chloroform solution was dried over anhydrous magnesium sulfate, concentrated and purified by the silica gel chromatography to obtain 3.0 g (77%) of the intended product (Compound No. 163), m.p. 98.0°~100.0° C. The elemental analysis of the product was effected with the results shown below.

| Results of Elemental Analysis ($C_{20}H_{24}N_2O_4S_1$) | | | | |
|---|---|---|---|---|
| | C | H | N | S |
| Calculated | 61.83 | 6.23 | 7.21 | 8.25 |
| Found | 61.78 | 6.25 | 7.19 | 8.30 |

In the similar manner as in Synthetic Example 10, there were obtained Compound Nos. 164~166 of Table 1. The chemical structures of these compounds were, respectively, confirmed by the I.R. spectrum and N.M.R. spectrum analysis.

TABLE 1

| Compound No. | Structure | | | | | | | | Melting point or refractive index |
|---|---|---|---|---|---|---|---|---|---|
| | $R^1$ | $R^2$ | $R^3$ | $R^4$ | $R^5$ | $R^6$ | $R^7$ | n | |
| 1 | $CH_3$ | $CH_3$ | H | H | H | H | H | 0 | $n_D^{25.0}$ 1.5270 |
| 2 | $ClCH_2CH_2$ | " | " | " | " | " | " | " | $n_D^{25.0}$ 1.5289 |
| 3 | n-$C_3H_7$ | " | " | " | " | " | " | " | $n_D^{25.0}$ 1.5205 |
| 4 | n-$C_4H_9$ | " | " | " | " | " | " | " | $n_D^{25.0}$ 1.5180 |
| 5 | ⌬—$CH_2$— | " | " | " | " | " | " | " | $n_D^{25.0}$ 1.5666 |

TABLE 1-continued
| Compound No. | Structure R¹ | R² | R³ | R⁴ | R⁵ | R⁶ | R⁷ | n | Melting point or refractive index |
|---|---|---|---|---|---|---|---|---|---|
| 6 |  | " | " | " | " | " | " | " | m.p 69.0~70.0 |
| 7 |  | " | " | " | " | " | " | " | m.p 46.5~48.0 |
| 8 |  | " | " | " | " | " | " | " | $n_D^{22.5}$ 1.5704 |
| 9 |  | " | " | " | " | " | " | " | $n_D^{24.0}$ 1.5660 |
| 10 |  | " | " | " | " | " | " | " | m.p 92.0~93.5 |
| 11 |  | " | " | " | " | " | " | " | $n_D^{25.0}$ 1.5606 |
| 12 |  | " | " | " | " | " | " | " | m.p 67.0~69.0 |
| 13 |  | " | " | " | " | " | " | " | $n_D^{26.5}$ 1.5648 |
| 14 |  | " | " | " | " | " | " | " | $n_D^{25.0}$ 1.5445 |
| 15 |  | " | " | " | " | " | " | " | $n_D^{24.5}$ 1.5438 |
| 16 |  | " | " | " | " | " | " | " | $n_D^{25.5}$ 1.5688 |
| 17 |  | " | " | " | " | " | " | " | m.p 77.0~78.5 |
| 18 |  | " | " | " | " | " | " | " | $n_D^{22.5}$ 1.5688 |
| 19 |  | " | " | " | " | " | " | " | $n_D^{24.5}$ 1.5582 |
| 20 | 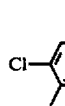 | " | " | " | " | " | " | " | $n_D^{25.0}$ 1.5863 |

TABLE 1-continued

| Compound No. | R¹ (Structure) | R² | R³ | R⁴ | R⁵ | R⁶ | R⁷ | n | Melting point or refractive index |
|---|---|---|---|---|---|---|---|---|---|
| 21 | 4-Cl-2,5-(CH₃)₂-C₆H₂— | " | " | " | " | " | " | " | $n_D^{25.0}$ 1.5882 |
| 22 | 4-Br-2,5-(CH₃)₂-C₆H₂— | " | " | " | " | " | " | " | $n_D^{25.0}$ 1.5741 |
| 23 | 4-HO-2,6-(CH₃)₂-C₆H₂— (with 3-CH₃) | " | " | " | " | " | " | " | m.p 169.0~171.0 |
| 24 | 4-CH₃O-2,6-(CH₃)₂-C₆H₂— | " | " | " | " | " | " | " | m.p 94.0~96.0 |
| 25 | 4-F-C₆H₄— | " | " | " | " | " | " | " | $n_D^{21.0}$ 1.5449 |
| 26 | 2-Cl-C₆H₄— | " | " | " | " | " | " | " | $n_D^{25.5}$ 1.5790 |
| 27 | 3-Cl-C₆H₄— | " | " | " | " | " | " | " | $n_D^{26.6}$ 1.5747 |
| 28 | 4-Cl-C₆H₄— | " | " | " | " | " | " | " | m.p 77.0~80.0 |
| 29 | 4-Br-C₆H₄— | " | " | " | " | " | " | " | m.p 113.5~118.0 |
| 30 | 4-Br-C₆H₄— | " | " | " | " | " | " | " | m.p 106.0~110.5 |
| 31 | 2,4,5-Cl₃-C₆H₂— | " | " | " | " | " | " | " | m.p 89.5~91.5 |
| 32 | 2,4,5-Cl₃-C₆H₂— | " | " | " | " | " | " | " | m.p 105.5~107.5 |
| 33 | 2-NO₂-C₆H₄— | " | " | " | " | " | " | " | $n_D^{26.5}$ 1.5572 |
| 34 | 3-O₂N-C₆H₄— | " | " | " | " | " | " | " | $n_D^{25.0}$ 1.5756 |

TABLE 1-continued

| Compound No. | Structure R¹ | R² | R³ | R⁴ | R⁵ | R⁶ | R⁷ | n | Melting point or refractive index |
|---|---|---|---|---|---|---|---|---|---|
| 35 | O₂N—⟨⟩— | " | " | " | " | " | " | " | m.p 108.0~110.0 |
| 36 | CH₃CO—⟨⟩— | " | " | " | " | " | " | " | $n_D^{23.5}$ 1.5786 |
| 37 | HO—⟨⟩— | " | " | " | " | " | " | " | m.p 82.0~86.0 |
| 38 | CH₃O—⟨⟩— | " | " | " | " | " | " | " | m.p 68.0~72.0 |
| 39 | C₂H₅O—⟨⟩— | " | " | " | " | " | " | " | m.p 84.0~87.0 |
| 40 | n-C₃H₇O—⟨⟩— | " | " | " | " | " | " | " | m.p 68.0~72.0 |
| 41 | iso-C₃H₇O—⟨⟩— | " | " | " | " | " | " | " | $n_D^{25.0}$ 1.5336 |
| 42 | n-C₄H₉O—⟨⟩— | " | " | " | " | " | " | " | $n_D^{25.0}$ 1.5468 |
| 43 | CH₂=CH—CH₂—O—⟨⟩— | " | " | " | " | " | " | " | m.p 57.0~61.0 |
| 44 | (epoxide)CH₂O—⟨⟩— | " | " | " | " | " | " | " | $n_D^{25.0}$ 1.5690 |
| 45 | Ph-CH(CH₃)-O—⟨⟩— | " | " | " | " | " | " | " | $n_D^{25.0}$ 1.5589 |
| 46 | ⟨⟩—CH₂O—⟨⟩— | " | " | " | " | " | " | " | m.p 95.0~98.0 |
| 47 | ClCH₂O—⟨⟩— | " | " | " | " | " | " | " | $n_D^{25.5}$ 1.5598 |
| 48 | ClCH₂CH₂O—⟨⟩— | " | " | " | " | " | " | " | m.p 99.0~101.0 |
| 49 | CH₃OCH₂O—⟨⟩— | " | " | " | " | " | " | " | $n_D^{26.0}$ 1.5493 |
| 50 | C₂H₅OCH₂O—⟨⟩— | " | " | " | " | " | " | " | $n_D^{26.0}$ 1.5336 |
| 51 | C₂H₅OC(O)—⟨⟩— | " | " | " | " | " | " | " | $n_D^{25.0}$ 1.5328 |
| 52 | CH₃NHC(O)—⟨⟩— | " | " | " | " | " | " | " | $n_D^{26.0}$ 1.5507 |
| 53 | C₂H₅NHC(O)—⟨⟩— | " | " | " | " | " | " | " | $n_D^{26.0}$ 1.5458 |

TABLE 1-continued

| Compound No. | R¹ | R² | R³ | R⁴ | R⁵ | R⁶ | R⁷ | n | Melting point or refractive index |
|---|---|---|---|---|---|---|---|---|---|
| 54 | n-C₃H₇NHC(O)O—⟨C₆H₄⟩— | " | " | " | " | " | " | " | $n_D^{25.5}$ 1.5410 |
| 55 | iso-C₃H₇NHC(O)O—⟨C₆H₄⟩— | " | " | " | " | " | " | " | $n_D^{25.5}$ 1.5357 |
| 56 | n-C₄H₉NHC(O)O—⟨C₆H₄⟩— | " | " | " | " | " | " | " | $n_D^{26.0}$ 1.5356 |
| 57 | (CH₃)₂NC(O)O—⟨C₆H₄⟩— | " | " | " | " | " | " | " | $n_D^{26.0}$ 1.5320 |
| 58 | (C₂H₅)₂NC(O)O—⟨C₆H₄⟩— | " | " | " | " | " | " | " | $n_D^{26.5}$ 1.5390 |
| 59 | C₂H₅OC(O)CH₂O—⟨C₆H₄⟩— | " | " | " | " | " | " | " | $n_D^{26.5}$ 1.5348 |
| 60 | C₂H₅OCO—CH(CH₃)—O—⟨C₆H₄⟩— | " | " | " | " | " | " | " | $n_D^{26.5}$ 1.5372 |
| 61 | CH₃(Ph)NC(O)O—⟨C₆H₄⟩— | " | " | " | " | " | " | " | $n_D^{26.5}$ 1.5472 |
| 62 | (CH₃)₂NSO₃—⟨C₆H₄⟩— | " | " | " | " | " | " | " | $n_D^{26.5}$ 1.5424 |
| 63 | CH₃SO₃—⟨C₆H₄⟩— | " | " | " | " | " | " | " | m.p 106.0~110.0 |
| 64 | C₂H₅SO₃—⟨C₆H₄⟩— | " | " | " | " | " | " | " | $n_D^{26.5}$ 1.5531 |
| 65 | n-C₃H₇SO₃—⟨C₆H₄⟩— | " | " | " | " | " | " | " | $n_D^{26.5}$ 1.5500 |
| 66 | O₂N—⟨C₆H₄⟩—O—⟨C₆H₄⟩— | " | " | " | " | " | " | " | m.p 90.0~95.0 |
| 67 | (6-Cl-pyridin-2-yl)—O—⟨C₆H₄⟩— | " | " | " | " | " | " | " | $n_D^{26.5}$ 1.5902 |
| 68 | 2-Cl-C₆H₄—CH₂O—⟨C₆H₄⟩— | " | " | " | " | " | " | " | $n_D^{26.5}$ 1.5737 |
| 69 | 4-Cl-C₆H₄—CH₂O—⟨C₆H₄⟩— | " | " | " | " | " | " | " | m.p 116.0~121.0 |

TABLE 1-continued

| Compound No. | R¹ | R² | R³ | R⁴ | R⁵ | R⁶ | R⁷ | n | Melting point or refractive index |
|---|---|---|---|---|---|---|---|---|---|
| 70 | 2,4-Cl₂-C₆H₃-CH₂O-C₆H₄- | " | " | " | " | " | " | " | m.p 113.0~118.0 |
| 71 | 3,4-Cl₂-C₆H₃-CH₂O-C₆H₄- | " | " | " | " | " | " | " | m.p 110.0~116.0 |
| 72 | CH₃-C₆H₄-CH₂O-C₆H₄- | " | " | " | " | " | " | " | m.p 107.0~111.0 |
| 73 | C₂H₅-C₆H₄-CH₂O-C₆H₄- | " | " | " | " | " | " | " | $n_D^{26.5}$ 1.5804 |
| 74 | iso-C₃H₇-C₆H₄-CH₂O-C₆H₄- | " | " | " | " | " | " | " | $n_D^{26.5}$ 1.5724 |
| 75 | HO-C₆H₄- | " | " | " | " | " | " | " | $n_D^{26.5}$ 1.5768 |
| 76 | C₆H₅-C(O)O-C₆H₄- | " | " | " | " | " | " | " | $n_D^{26.5}$ 1.5792 |
| 77 | C₂H₅O-C₆H₄- | " | " | " | " | " | " | " | $n_D^{26.5}$ 1.5617 |
| 78 | n-C₃H₇O-C₆H₄- | " | " | " | " | " | " | " | $n_D^{26.5}$ 1.5536 |
| 79 | glycidyloxy-C₆H₄- | " | " | " | " | " | " | " | $n_D^{26.5}$ 1.5649 |
| 80 | n-C₃H₇-C₆H₄- | " | " | O—Cl | " | " | " | " | $n_D^{26.0}$ 1.5612 |
| 81 | " | " | " | m-Cl | " | " | " | " | $n_D^{26.0}$ 1.5647 |
| 82 | " | " | " | P—Cl | " | " | " | " | m.p 97.5~99.0 |
| 83 | " | " | " | H | " | CH₃ | " | " | $n_D^{25.0}$ 1.5433 |
| 84 | " | " | " | " | CH₃ | H | " | " | $n_D^{25.0}$ 1.5553 |
| 85 | " | " | " | " | H | CH₃ | CH₃ | " | $n_D^{25.0}$ 1.5463 |
| 86 | " | " | " | " | " | Ph | H | " | $n_D^{25.0}$ 1.5703 |
| 87 | " | " | " | " | " | ClCH₂ | " | " | $n_D^{25.0}$ 1.5677 |
| 88 | C₆H₅- | " | " | " | CH₃ | H | " | " | $n_D^{26.5}$ 1.5426 |
| 89 | " | " | " | " | H | CH₃ | " | " | $n_D^{26.5}$ 1.5527 |
| 90 | " | C₂H₅ | " | " | " | H | " | " | $n_D^{26.5}$ 1.5582 |

TABLE 1-continued

| Compound No. | R¹ | R² | R³ | R⁴ | R⁵ | R⁶ | R⁷ | n | Melting point or refractive index |
|---|---|---|---|---|---|---|---|---|---|
| 91 | 2-Cl-C₆H₄- | " | " | " | " | " | " | " | $n_D^{24.5}$ 1.5765 |
| 92 | 4-CH₃-C₆H₄- | " | " | " | " | " | " | " | $n_D^{26.0}$ 1.5548 |
| 93 | 4-C₂H₅-C₆H₄- | " | " | " | " | " | " | " | $n_D^{26.5}$ 1.5477 |
| 94 | 4-n-C₃H₇-C₆H₄- | " | " | " | " | " | " | " | $n_D^{26.5}$ 1.5407 |
| 95 | 4-iso-C₃H₇-C₆H₄- | " | " | " | " | " | " | " | $n_D^{26.5}$ 1.5438 |
| 96 | C₆H₅- | n-C₃H₇ | " | " | " | " | " | " | $n_D^{26.5}$ 1.5563 |
| 97 | 4-CH₃-C₆H₄- | " | " | " | " | " | " | " | $n_D^{26.5}$ 1.5516 |
| 98 | 4-C₂H₅-C₆H₄- | " | " | " | " | " | " | " | $n_D^{26.5}$ 1.5456 |
| 99 | C₆H₅- | iso-C₃H₇ | " | " | " | " | " | " | $n_D^{26.5}$ 1.5494 |
| 100 | 4-CH₃-C₆H₄- | " | " | " | " | " | " | " | m.p 80.0~85.0 |
| 101 | 4-C₂H₅-C₆H₄- | " | " | " | " | " | " | " | $n_D^{26.0}$ 1.5520 |
| 102 | 4-CH₃-C₆H₄- | " | CH₃ | " | " | " | " | " | m.p 76.0~77.0 |
| 103 | 4-C₂H₅-C₆H₄- | " | " | " | " | " | " | " | $n_D^{26.5}$ 1.5608 |
| 104 | 4-n-C₃H₇-C₆H₄- | " | " | " | " | " | " | " | m.p 73.0~74.0 |
| 105 | 4-iso-C₃H₇-C₆H₄- | CH₃ | " | " | " | " | " | " | $n_D^{26.5}$ 1.5407 |
| 106 | 2-CH₃-C₆H₄- | " | " | " | " | " | " | " | m.p 73.5~76.5 |
| 107 | 4-CH₃-C₆H₄- | " | " | " | " | " | " | " | m.p 71.5~74.5 |
| 108 | 2-CH₃-4-CH₃-C₆H₃- | " | " | " | " | " | " | " | m.p 110.0~113.5 |

TABLE 1-continued

| Compound No. | R¹ | Structure R² | R³ | R⁴ | R⁵ | R⁶ | R⁷ | n | Melting point or refractive index |
|---|---|---|---|---|---|---|---|---|---|
| 109 | 2-Cl-C₆H₄- | " | " | " | " | " | " | " | m.p 117.5~124.0 |
| 110 | 4-(n-C₃H₇)-C₆H₄- | " | " | " | " | CH₃ | " | " | $n_D^{25.0}$ 1.5507 |
| 111 | " | " | " | " | " | " | CH₃ | " | $n_D^{25.0}$ 1.5536 |
| 112 | C₆H₅- | " | " | " | CH₃ | H | H | " | m.p 106.0~108.0 |
| 113 | " | " | " | " | H | CH₃ | " | " | $n_D^{26.5}$ 1.5504 |
| 114 | 4-F-C₆H₄- | " | " | " | " | H | " | 1 | $n_D^{26.5}$ 1.5360 |
| 115 | 4-C₂H₅-C₆H₄- | " | " | " | " | " | " | 1 | $n_D^{26.5}$ 1.5514 |
| 116 | 4-(n-C₃H₇)-C₆H₄- | " | " | " | " | " | " | 1 | $n_D^{26.5}$ 1.5270 |
| 117 | 4-(iso-C₃H₇)-C₆H₄- | " | " | " | " | " | " | 1 | $n_D^{26.5}$ 1.5245 |
| 118 | C₆H₅- | H | H | " | " | " | " | 1 | $n_D^{26.5}$ 1.5521 |
| 119 | " | CH₃ | " | 2-CH₃, 5-CH₃ | " | " | " | 0 | $n_D^{23.5}$ 1.5630 |
| 120 | 4-CH₃-C₆H₄- | " | " | " | " | " | " | " | m.p 88~89 |
| 121 | 4-(s-C₄H₉)-C₆H₄- | " | " | H | " | " | " | " | $n_D^{25.5}$ 1.5498 |
| 122 | 4-(t-C₄H₉)-C₆H₄- | " | " | " | " | " | " | " | $n_D^{24.5}$ 1.5517 |
| 123 | 4-(n-C₅H₁₁)-C₆H₄- | " | " | " | " | " | " | " | $n_D^{25.5}$ 1.5483 |
| 124 | 4-(s-C₅H₁₁)-C₆H₄- | " | " | " | " | " | " | " | $n_D^{25.5}$ 1.5478 |
| 125 | 4-(i-C₄H₉)-C₆H₄- | " | " | " | " | " | " | " | $n_D^{25.5}$ 1.5504 |
| 126 | 4-(t-C₅H₁₁)-C₆H₄- | " | " | " | " | " | " | " | m.p 65.0~66.0 |
| 127 | 3,4-(CH₃)₂-C₆H₃- | " | " | " | " | " | " | " | Amorphous |

TABLE 1-continued
| Compound No. | R¹ | R² | R³ | R⁴ | R⁵ | R⁶ | R⁷ | n | Melting point or refractive index |
|---|---|---|---|---|---|---|---|---|---|
| 128 | 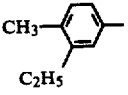 | " | " | " | " | " | " | " | $n_D^{25.0}$ 1.5615 |
| 129 | 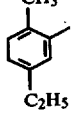 | " | " | " | " | " | " | " | $n_D^{25.0}$ 1.5659 |
| 130 | 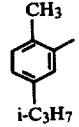 | " | " | " | " | " | " | " | $n_D^{25.0}$ 1.5497 |
| 131 | 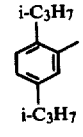 | " | " | " | " | " | " | " | $n_D^{25.5}$ 1.5451 |
| 132 | 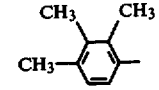 | " | " | " | " | " | " | " | m.p 87.0~89.0 |
| 133 | 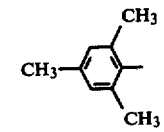 | " | " | " | " | " | " | " | m.p 107.0~108.0 |
| 134 | 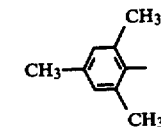 | " | " | " | " | " | " | " | m.p 90.0~92.0 |
| 135 | 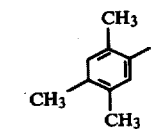 | " | " | " | " | " | " | " | m.p 94.5~95.5 |
| 136 | 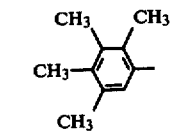 | " | " | " | " | " | " | " | m.p 83.0~84.0 |
| 137 | 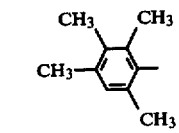 | " | " | " | " | " | " | " | $n_D^{25.0}$ 1.5625 |
| 138 | 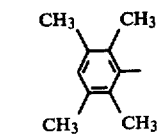 | " | " | " | " | " | " | " | $n_D^{26.0}$ 1.5650 |
| 139 | 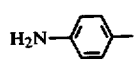 | " | " | " | " | " | " | " | m.p 120~121 |

TABLE 1-continued

| Compound No. | R¹ (Structure) | R² | R³ | R⁴ | R⁵ | R⁶ | R⁷ | n | Melting point or refractive index |
|---|---|---|---|---|---|---|---|---|---|
| 140 | CH₃CONH—⟨C₆H₄⟩— | " | " | " | " | " | " | " | $n_D^{27.0}$ 1.5770 |
| 141 | CH₃OC(O)NH—⟨C₆H₄⟩— | " | " | " | " | " | " | " | $n_D^{24.5}$ 1.5678 |
| 142 | (CH₃)(CH₃O)NC(O)NH—⟨C₆H₄⟩— | " | " | " | " | " | " | " | m.p 74~75 |
| 143 | C₂H₅OC(O)CH(CH₃)NH—⟨C₆H₄⟩— | " | " | " | " | " | " | " | $n_D^{24.5}$ 1.5688 |
| 144 | H₂N—⟨C₆H₄⟩— (meta) | " | " | " | " | " | " | " | m.p 115~116 |
| 145 | CH₃CONH—⟨C₆H₄⟩— (meta) | " | " | " | " | " | " | " | Amorphous |
| 146 | CH₃OC(O)NH—⟨C₆H₄⟩— (meta) | " | " | " | " | " | " | " | $n_D^{24.5}$ 1.5458 |
| 147 | (CH₃)(CH₃O)NC(O)NH—⟨C₆H₄⟩— (meta) | " | " | " | " | " | " | " | Amorphous |
| 148 | C₂H₅OC(O)CH(CH₃)NH—⟨C₆H₄⟩— (meta) | " | " | " | " | " | " | " | $n_D^{25.0}$ 1.5521 |
| 149 | NH₂—⟨C₆H₄⟩— (ortho) | " | " | " | " | " | " | " | m.p 127~130 |
| 150 | NHCOCH₃—⟨C₆H₄⟩— (ortho) | " | " | " | " | " | " | " | m.p 181~184 |
| 151 | indenyl— | " | " | " | " | " | " | " | $n_D^{25.5}$ 1.5772 |
| 152 | tetrahydronaphthyl— | " | " | " | " | " | " | " | $n_D^{24.5}$ 1.5982 |
| 153 | cyclopentyl-phenyl— | " | " | " | " | " | " | " | $n_D^{24.5}$ 1.5695 |
| 154 | cyclohexyl-phenyl— | " | " | " | " | " | " | " | $n_D^{25.0}$ 1.5648 |

TABLE 1-continued

| Compound No. | R¹ (Structure) | R² | R³ | R⁴ | R⁵ | R⁶ | R⁷ | n | Melting point or refractive index |
|---|---|---|---|---|---|---|---|---|---|
| 155 | 4-CH₃, 3-CH₃-cyclohexylphenyl (H) | " | " | " | " | " | " | " | $n_D^{26.0}$ 1.5630 |
| 156 | 2-CH₃, 4-CH₃-cyclohexylphenyl (H) | " | " | " | " | " | " | " | $n_D^{26.0}$ 1.5500 |
| 157 | 4-cycloheptylphenyl (H) | " | " | " | " | " | " | " | $n_D^{24.5}$ 1.5622 |
| 158 | CH₃NHCOO-phenyl (m-) | " | " | " | " | " | " | " | m.p 76~78 |
| 159 | n-C₃H₇NHCOO-phenyl (m-) | " | " | " | " | " | " | " | m.p 79~80 |
| 160 | (CH₃)₂CH-NHCOO-phenyl (m-) | " | " | " | " | " | " | " | m.p 104~106 |
| 161 | (CH₃)₂NCOO-phenyl (m-) | " | " | " | " | " | " | " | m.p 119~121 |
| 162 | (C₂H₅)₂NCOO-phenyl (m-) | " | " | " | " | " | " | " | m.p 56~57 |
| 163 | (CH₃)₂NCO-phenyl (p-) | " | " | " | " | " | " | " | m.p 98~100 |
| 164 | (C₂H₅)₂NCO-phenyl (p-) | " | " | " | " | " | " | " | m.p 80~81 |
| 165 | (i-C₃H₇)₂NCO-phenyl (p-) | " | " | " | " | " | " | " | $n_D^{24.5}$ 1.5330 |
| 166 | (n-C₄H₉)₂NCO-phenyl (p-) | " | " | " | " | " | " | " | $n_D^{24.5}$ 1.5378 |
| 167 | phenyl | " | " | 2,5-di(CH₃) | " | " | " | " | $n_D^{25}$ 1.5698 |
| 168 | CH₃-phenyl (p-) | " | " | " | " | " | " | " | m.p 91~93 |

TABLE 1-continued

| Compound No. | R¹ | Structure R² | R³ | R⁴ | R⁵ | R⁶ | R⁷ | n | Melting point or refractive index |
|---|---|---|---|---|---|---|---|---|---|
| 169 | 2,4-(CH₃)₂-C₆H₃- | " | " | " | " | " | " | " | $n_D^{24.5}$ 1.5646 |
| 170 | i-C₃H₇-C₆H₄- | " | " | " | " | " | " | " | $n_D^{24.5}$ 1.5561 |
| 171 | CH₃O-C₆H₄- | " | " | " | " | " | " | " | $n_D^{24.5}$ 1.5670 |
| 172 | C₆H₅- | " | " | 4-CH₃O | " | " | " | " | $n_D^{24.5}$ 1.5555 |
| 173 | n-C₃H₇-C₆H₄- | " | " | " | " | " | " | " | $n_D^{24.5}$ 1.5509 |
| 174 | i-C₃H₇-C₆H₄- | " | " | " | " | " | " | " | $n_D^{24.5}$ 1.5499 |
| 175 | t-C₄H₉-C₆H₄- | " | " | " | " | " | " | " | $n_D^{24.5}$ 1.5402 |
| 176 | 2-CH₃-C₆H₄- | " | " | " | " | " | " | " | $n_D^{24.5}$ 1.5639 |
| 177 | Cl-C₆H₄- | " | " | " | " | " | " | " | m.p 92~93 |
| 178 | C₆H₅- | " | " | 3-CH₃O | " | " | " | " | m.p 87~88 |
| 179 | CH₃O-C₆H₄- | " | " | " | " | " | " | " | m.p 76~77 |
| 180 | CH₃-C₆H₄- | " | " | " | " | " | " | " | m.p 67~68 |
| 181 | n-C₃H₇-C₆H₄- | " | " | " | " | " | " | " | m.p 55~56 |
| 182 | i-C₃H₇-C₆H₄- | " | " | " | " | " | " | " | m.p 69~71 |
| 183 | t-C₄H₉-C₆H₄- | " | " | " | " | " | " | " | m.p 87~89 |
| 184 | 2-CH₃-C₆H₄- | " | " | " | " | " | " | " | m.p 70~73 |
| 185 | Cl-C₆H₄- | " | " | " | " | " | " | " | m.p 63~64 |
| 186 | C₆H₅- | " | " | 2-CH₃O | " | " | " | " | m.p 103~105 |

TABLE 1-continued

| Compound No. | R¹ | R² | R³ | R⁴ | R⁵ | R⁶ | R⁷ | n | Melting point or refractive index |
|---|---|---|---|---|---|---|---|---|---|
| 187 | CH₃O—⟨C₆H₄⟩— | " | " | " | " | " | " | " | $n_D^{24.5}$ 1.5592 |
| 188 | CH₃—⟨C₆H₄⟩— | " | " | " | " | " | " | " | m.p 68~70 |
| 189 | n-C₃H₇—⟨C₆H₄⟩— | " | " | " | " | " | " | " | m.p 93~95 |
| 190 | 2-CH₃—C₆H₄— | " | " | " | " | " | " | " | m.p 48~49 |
| 191 | Cl—⟨C₆H₄⟩— | " | " | " | " | " | " | " | m.p 104~106 |
| 192 | C₆H₅— | " | " | 4-CH₃ | " | " | " | " | m.p 69~70 |
| 193 | 2-CH₃—C₆H₄— | " | " | " | " | " | " | " | $n_D^{24.5}$ 1.5575 |
| 194 | CH₃—⟨C₆H₄⟩— | " | " | " | " | " | " | " | m.p 79~80 |
| 195 | i-C₃H₇—⟨C₆H₄⟩— | " | " | " | " | " | " | " | $n_D^{24.5}$ 1.5489 |
| 196 | t-C₄H₉—⟨C₆H₄⟩— | " | " | " | " | " | " | " | m.p 68~70 |
| 197 | CH₃O—⟨C₆H₄⟩— | " | " | " | " | " | " | " | m.p 69~71 |
| 198 | 3-Cl—C₆H₄— | " | " | " | " | " | " | " | $n_D^{24.5}$ 1.5663 |
| 199 | C₆H₅— | " | " | " | " | " | " | " | $n_D^{24.5}$ 1.5660 |
| 200 | i-C₃H₇—⟨C₆H₄⟩— | " | " | " | " | " | " | " | $n_D^{24.5}$ 1.5442 |
| 201 | 2,4,6-(CH₃)₃—C₆H₂— | " | " | " | " | " | " | " | $n_D^{24.5}$ 1.5552 |
| 202 | CH₃O—⟨C₆H₄⟩— | " | " | " | " | " | " | " | m.p 58~60 |
| 203 | C₆H₅— | " | " | 3-CH₃ | " | " | " | " | $n_D^{24.5}$ 1.5592 |

TABLE 1-continued

| Compound No. | R¹ | R² | R³ | R⁴ | R⁵ | R⁶ | R⁷ | n | Melting point or refractive index |
|---|---|---|---|---|---|---|---|---|---|
| 204 | 2-CH₃-C₆H₄- | " | " | " | " | " | " | " | $n_D^{24.5}$ 1.5558 |
| 205 | 4-CH₃-C₆H₄- | " | " | " | " | " | " | " | $n_D^{24.5}$ 1.5568 |
| 206 | 4-i-C₃H₇-C₆H₄- | " | " | " | " | " | " | " | $n_D^{24.5}$ 1.5565 |
| 207 | 4-t-C₄H₉-C₆H₄- | " | " | " | " | " | " | " | $n_D^{24.5}$ 1.5402 |
| 208 | 2,4,6-(CH₃)₃-C₆H₂- | " | " | " | " | " | " | " | m.p 73~75 |
| 209 | 4-CH₃O-C₆H₄- | " | " | " | " | " | " | " | $n_D^{24.5}$ 1.5509 |
| 210 | 2,4,6-(CH₃)₃-C₆H₂- | " | " | 4-CH₃O | " | " | " | " | $n_D^{24.5}$ 1.5570 |
| 211 | 2,4,6-(CH₃)₃-C₆H₂- | " | " | 3-CH₃O | " | " | " | " | m.p 84~85 |
| 212 | 2,4,6-(CH₃)₃-C₆H₂- | " | " | 2-CH₃O | " | " | " | " | m.p 87~88 |

In the following Preparation Examples, parts and percentages are by weight unless otherwise indicated.

Preparation Example 1 (Wettable Powder)

40 parts of Compound No. 10 indicated in Table 1, 20 parts of Carplex (trade name, by Shionogi Pharm. Co., Ltd.), 35 parts of N,N Kaolin Clay (trade name, by Tsuchiya Kaolin K.K.) and 5 parts of a higher alcohol sulfuric ester surfactant, Sorpol 8070 (trade name, by Toho Chem. Co., Ltd.) were uniformly mixed and ground to pieces to obtain a wettable powder having 40% of the effective ingredient.

Preparation Example 2 (Granular)

5 parts of Compound No. 14 indicated in Table 1, 38 parts of clay (by Nippon Talc Co., Ltd.), 55 parts of bentonite (by Hojun Yoko Co., Ltd.), and 2 parts of a succinate surfactant, Airrol CT-1 (trade name, by Toho Chem. Co., Ltd.) were mixed and ground into pieces, after which 10 parts of water were added. The mixture was uniformly agitated and extruded through the screen, each screen having a diameter of 0.7 mm, of a kneading and granulating machine, followed by drying at 60° C. for 2 hours and cutting the extrudate into pieces having a length of 1~2 mm thereby obtaining a granular product having 5% of the effective ingredient.

Preparation Example 3 (Emulsion)

30 parts of Compound No. 104 indicated in Table 1 was dissolved in a mixed solvent of 30 parts of xylene and 25 parts of dimethylformamide, to which was added 15 parts of a polyoxyethylene surfactant, Sorpol 3005X (trade name, by Toho Chem. Co., Ltd.) thereby obtaining an emulsion containing 30% of the effective ingredient.

Preparation Example 4 (Dust)

5 parts of Compound No. 17 indicated in Table 1, 10 parts of clay, Whiten TOKUSETU (trade name, by Showa Minerals Co., Ltd.) were mixed and ground to obtain a concentrate powder, to which was added 85 parts of the clay, followed by milling to obtain a dust containing 5% of the effective ingredient.

When the starting compound was in the form of a liquid, the dust was prepared as follows. 5 parts of Compound No. 15 indicated in Table 1 was adsorbed on 10 parts of Carplex #80 (trade name, by Shionogi Pharm. Co., Ltd.), followed by mixing and ground to obtain a concentrate powder. 85 parts of clay, Whiten TOKUSETU (trade name, by Showa Minerals Co., Ltd.) was added to that concentrated powder, followed by milling to obtain a dust containing 5% of the effective ingredient.

In the following Experimental Examples, the weeds used are abbreviated as follows.

| | |
|---|---|
| Barnyardgrass (*Echinochloa crus-galli*) | E.C. |
| Tooth cup (*Rotala indica*) | R.I. |
| Smallflower umbrellaplant (*Cyperus difformis*) | C.D. |
| Hardstem bulrush (*Scirpus juncoides*) | S.J. |
| Ducktongue weed (*Monochoria vaginalis*) | M.V. |
| Large crabgrass (*Digitaria sanguinalis*) | D.S. |
| Umbrella sedge (*Cyperus microiria*) | C.M. |

The following known compounds were used for comparative purposes.

| | |
|---|---|
| Agent A: | N—allyl-N—(α,α-dimethylbenzyl)benzene-sulfonamide |
| Agent B: | N—allyl-N—(α-methylbenzyl)benzene-sulfonamide |
| Agent C: | S—(4-chlorobenzyl)-N,N—diethylthiocarbamate |
| Agent D: | 3-(3,4-dichlorophenyl)-1,1-dimethylurea |

Experimental Example 1

Submerged Soil Test Before Emergence of Paddy Weeds

Paddy alluvial clayish loam was charged in each of resin vats having an area of 1/2500 are and was applied with a fertilizer, after which seeds of barnyardgrass, toothcup, smallflower umbrellaplant and hardstem bulrush were sowed. The seeds were well mixed within 1 cm of the soil surface layer and the submerged condition was maintained at a depth of about 3 cm. Next day, the wettable powders containing the compounds in Table below as an effective component obtained in Preparation Example 1 were diluted with water and applied by dropping the dilutions to the surface of water in such amounts of 50, 25, 12.5 and 6.25 g per are. Thereafter, the vats were managed in a greenhouse and the herbicidal effect was checked at 28th day after the treatment with the herbicides. The results are shown in Table 2.

The herbicidal activity was evaluated as follows: the Y value was obtained according to the following equation, $$\left(1 - \frac{\text{fresh weight of vegetative part of weeds in treated plot}}{\text{fresh weight of vegetative part of weeds in non-treated plot}}\right) \times 100 = Y(\%)$$

and the effect was evaluated in terms of a coefficient for the herbicidal effect based on the following standard.

| Coefficient for Herbicidal Effect | Y (%) |
|---|---|
| 0 | 0–4 |
| 1 | 5–29 |
| 2 | 30–49 |
| 3 | 50–69 |
| 4 | 70–89 |
| 5 | 90–100 |

TABLE 2

| Compound No. | Dose g/a | Herbicidal effect E.C. | R.I. | C.D. | S.J. |
|---|---|---|---|---|---|
| 1 | 50 | 5 | 5 | 5 | 5 |
|   | 25 | 5 | 5 | 5 | 5 |
|   | 12.5 | 4 | 4 | 5 | 3 |
|   | 6.25 | 4 | 3 | 4 | 3 |
| 2 | 50 | 5 | 5 | 5 | 5 |
|   | 25 | 5 | 5 | 5 | 5 |
|   | 12.5 | 4 | 5 | 5 | 4 |
|   | 6.25 | 4 | 4 | 5 | 3 |
| 3 | 50 | 5 | 5 | 5 | 5 |
|   | 25 | 5 | 5 | 5 | 5 |
|   | 12.5 | 5 | 4 | 4 | 4 |
|   | 6.25 | 4 | 3 | 3 | 2 |
| 4 | 50 | 5 | 5 | 5 | 5 |
|   | 25 | 5 | 5 | 5 | 5 |
|   | 12.5 | 3 | 4 | 4 | 3 |
|   | 6.25 | 3 | 3 | 3 | 2 |
| 5 | 50 | 5 | 5 | 5 | 5 |
|   | 25 | 5 | 5 | 5 | 5 |
|   | 12.5 | 5 | 4 | 5 | 5 |
|   | 6.25 | 4 | 4 | 5 | 3 |
| 6 | 50 | 5 | 5 | 5 | 5 |
|   | 25 | 5 | 5 | 5 | 5 |
|   | 12.5 | 5 | 5 | 5 | 5 |
|   | 6.25 | 5 | 4 | 5 | 4 |
| 7 | 50 | 5 | 5 | 5 | 5 |
|   | 25 | 5 | 5 | 5 | 5 |
|   | 12.5 | 5 | 5 | 5 | 4 |
|   | 6.25 | 5 | 5 | 5 | 3 |
| 8 | 50 | 5 | 5 | 5 | 5 |
|   | 25 | 5 | 5 | 5 | 5 |
|   | 12.5 | 5 | 5 | 5 | 5 |
|   | 6.25 | 4 | 5 | 5 | 3 |
| 9 | 50 | 5 | 5 | 5 | 5 |
|   | 25 | 5 | 5 | 5 | 5 |
|   | 12.5 | 5 | 5 | 5 | 5 |
|   | 6.25 | 5 | 5 | 5 | 5 |
| 10 | 50 | 5 | 5 | 5 | 5 |
|   | 25 | 5 | 5 | 5 | 5 |
|   | 12.5 | 5 | 5 | 5 | 5 |
|   | 6.25 | 5 | 5 | 5 | 5 |
| 11 | 50 | 5 | 5 | 5 | 5 |
|   | 25 | 5 | 5 | 5 | 5 |
|   | 12.5 | 5 | 5 | 5 | 5 |
|   | 6.25 | 5 | 4 | 5 | 4 |
| 12 | 50 | 5 | 5 | 5 | 5 |
|   | 25 | 5 | 5 | 5 | 5 |
|   | 12.5 | 5 | 5 | 5 | 5 |
|   | 6.25 | 5 | 5 | 5 | 5 |
| 13 | 50 | 5 | 5 | 5 | 5 |
|   | 25 | 5 | 5 | 5 | 5 |
|   | 12.5 | 5 | 5 | 5 | 5 |
|   | 6.25 | 5 | 5 | 5 | 5 |
| 14 | 50 | 5 | 5 | 5 | 5 |
|   | 25 | 5 | 5 | 5 | 5 |
|   | 12.5 | 5 | 5 | 5 | 5 |
|   | 6.25 | 5 | 5 | 5 | 5 |
| 15 | 50 | 5 | 5 | 5 | 5 |
|   | 25 | 5 | 5 | 5 | 5 |
|   | 12.5 | 5 | 5 | 5 | 5 |
|   | 6.25 | 5 | 5 | 5 | 5 |
| 16 | 50 | 5 | 5 | 5 | 5 |
|   | 25 | 5 | 5 | 5 | 5 |
|   | 12.5 | 5 | 5 | 5 | 5 |
|   | 6.25 | 5 | 5 | 5 | 5 |
| 17 | 50 | 5 | 5 | 5 | 5 |
|   | 25 | 5 | 5 | 5 | 5 |
|   | 12.5 | 5 | 5 | 5 | 4 |
|   | 6.25 | 5 | 5 | 5 | 4 |
| 18 | 50 | 5 | 5 | 5 | 5 |

TABLE 2-continued

| Compound No. | Dose g/a | Herbicidal effect | | | |
|---|---|---|---|---|---|
| | | E.C. | R.I. | C.D. | S.J. |
| | 25 | 5 | 5 | 5 | 5 |
| | 12.5 | 4 | 5 | 5 | 4 |
| | 6.25 | 4 | 4 | 4 | 3 |
| 19 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 4 |
| 20 | 50 | 5 | 5 | 5 | 5 |
| | 25 | 5 | 5 | 5 | 4 |
| | 12.5 | 4 | 4 | 5 | 4 |
| | 6.25 | 3 | 4 | 4 | 3 |
| 21 | 50 | 5 | 5 | 5 | 5 |
| | 25 | 4 | 5 | 5 | 4 |
| | 12.5 | 4 | 4 | 5 | 3 |
| | 6.25 | 3 | 4 | 3 | 3 |
| 22 | 50 | 5 | 5 | 5 | 4 |
| | 25 | 5 | 5 | 5 | 4 |
| | 12.5 | 3 | 4 | 5 | 3 |
| | 6.25 | 3 | 4 | 4 | 2 |
| 23 | 50 | 5 | 5 | 5 | 5 |
| | 25 | 5 | 4 | 5 | 4 |
| | 12.5 | 4 | 4 | 4 | 3 |
| | 6.25 | 3 | 4 | 4 | 2 |
| 24 | 50 | 5 | 5 | 5 | 5 |
| | 25 | 5 | 5 | 5 | 4 |
| | 12.5 | 3 | 4 | 4 | 2 |
| | 6.25 | 2 | 3 | 3 | 2 |
| 25 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 5 |
| 26 | 50 | 5 | 5 | 5 | 5 |
| | 25 | 5 | 5 | 5 | 5 |
| | 12.5 | 5 | 5 | 5 | 4 |
| | 6.25 | 4 | 5 | 5 | 4 |
| 27 | 50 | 5 | 5 | 5 | 5 |
| | 25 | 5 | 5 | 5 | 5 |
| | 12.5 | 5 | 5 | 5 | 4 |
| | 6.25 | 5 | 5 | 5 | 4 |
| 28 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 5 |
| 29 | 50 | 5 | 5 | 5 | 4 |
| | 25 | 4 | 4 | 5 | 4 |
| | 12.5 | 4 | 4 | 5 | 2 |
| | 6.25 | 4 | 3 | 5 | 1 |
| 30 | 50 | 5 | 5 | 5 | 4 |
| | 25 | 4 | 5 | 5 | 3 |
| | 12.5 | 4 | 4 | 5 | 3 |
| | 6.25 | 3 | 3 | 4 | 1 |
| 31 | 50 | 4 | 4 | 5 | 3 |
| | 25 | 3 | 4 | 5 | 3 |
| | 12.5 | 3 | 3 | 4 | 1 |
| | 6.25 | 1 | 3 | 3 | 0 |
| 32 | 50 | 4 | 5 | 5 | 3 |
| | 25 | 2 | 4 | 5 | 1 |
| | 12.5 | 1 | 3 | 5 | 1 |
| | 6.25 | 0 | 3 | 4 | 0 |
| 33 | 50 | 5 | 5 | 5 | 5 |
| | 25 | 5 | 5 | 5 | 4 |
| | 12.5 | 4 | 5 | 5 | 3 |
| | 6.25 | 4 | 3 | 5 | 3 |
| 34 | 50 | 5 | 5 | 5 | 5 |
| | 25 | 5 | 5 | 5 | 5 |
| | 12.5 | 5 | 5 | 5 | 4 |
| | 6.25 | 4 | 4 | 5 | 4 |
| 35 | 50 | 5 | 5 | 5 | 5 |
| | 25 | 5 | 5 | 5 | 5 |
| | 12.5 | 4 | 4 | 5 | 5 |
| | 6.25 | 4 | 4 | 5 | 4 |
| 36 | 50 | 5 | 5 | 5 | 5 |
| | 25 | 5 | 5 | 5 | 5 |
| | 12.5 | 5 | 5 | 5 | 5 |
| | 6.25 | 4 | 5 | 5 | 5 |
| 37 | 50 | 5 | 5 | 5 | 5 |
| | 25 | 5 | 5 | 5 | 5 |
| | 12.5 | 5 | 5 | 5 | 5 |
| | 6.25 | 4 | 5 | 5 | 4 |
| 38 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 5 |
| 39 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 5 |
| 40 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 4 |
| 41 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 4 |
| 42 | 50 | 5 | 5 | 5 | 5 |
| | 25 | 5 | 5 | 5 | 4 |
| | 12.5 | 5 | 5 | 5 | 4 |
| | 6.25 | 4 | 5 | 5 | 3 |
| 43 | 50 | 5 | 5 | 5 | 5 |
| | 25 | 5 | 5 | 5 | 4 |
| | 12.5 | 5 | 5 | 5 | 3 |
| | 6.25 | 4 | 5 | 5 | 3 |
| 44 | 50 | 5 | 5 | 5 | 5 |
| | 25 | 5 | 5 | 5 | 4 |
| | 12.5 | 5 | 5 | 5 | 4 |
| | 6.25 | 4 | 5 | 5 | 3 |
| 45 | 50 | 5 | 5 | 5 | 4 |
| | 25 | 4 | 5 | 5 | 3 |
| | 12.5 | 4 | 5 | 5 | 3 |
| | 6.25 | 4 | 5 | 5 | 1 |
| 46 | 50 | 5 | 5 | 5 | 4 |
| | 25 | 4 | 5 | 5 | 4 |
| | 12.5 | 4 | 5 | 5 | 3 |
| | 6.25 | 3 | 5 | 5 | 3 |
| 47 | 50 | 4 | 5 | 5 | 4 |
| | 25 | 3 | 5 | 4 | 3 |
| | 12.5 | 3 | 3 | 4 | 1 |
| | 6.25 | 0 | 3 | 3 | 0 |
| 48 | 50 | 5 | 5 | 5 | 5 |
| | 25 | 5 | 5 | 5 | 4 |
| | 12.5 | 5 | 5 | 5 | 3 |
| | 6.25 | 4 | 5 | 5 | 2 |
| 49 | 50 | 3 | 5 | 5 | 3 |
| | 25 | 3 | 5 | 5 | 1 |
| | 12.5 | 1 | 4 | 3 | 0 |
| | 6.25 | 0 | 3 | 3 | 0 |
| 50 | 50 | 4 | 5 | 5 | 4 |
| | 25 | 3 | 5 | 5 | 3 |
| | 12.5 | 3 | 3 | 4 | 1 |
| | 6.25 | 1 | 3 | 4 | 0 |
| 51 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 4 |
| 52 | 50 | 5 | 5 | 5 | 5 |
| | 25 | 5 | 5 | 5 | 5 |
| | 12.5 | 5 | 5 | 5 | 4 |
| | 6.25 | 4 | 5 | 5 | 4 |
| 53 | 50 | 5 | 5 | 5 | 5 |
| | 25 | 5 | 5 | 5 | 5 |
| | 12.5 | 5 | 5 | 5 | 4 |
| | 6.25 | 5 | 5 | 5 | 4 |
| 54 | 50 | 5 | 5 | 5 | 5 |
| | 25 | 5 | 5 | 5 | 5 |
| | 12.5 | 5 | 5 | 5 | 4 |
| | 6.25 | 5 | 5 | 5 | 3 |
| 55 | 50 | 5 | 5 | 5 | 5 |
| | 25 | 5 | 5 | 5 | 5 |
| | 12.5 | 5 | 5 | 5 | 4 |
| | 6.25 | 4 | 4 | 5 | 3 |
| 56 | 50 | 5 | 5 | 5 | 5 |
| | 25 | 5 | 5 | 5 | 5 |
| | 12.5 | 5 | 5 | 5 | 3 |
| | 6.25 | 4 | 4 | 5 | 3 |
| 57 | 50 | 5 | 5 | 5 | 5 |
| | 25 | 5 | 5 | 5 | 5 |
| | 12.5 | 5 | 5 | 5 | 4 |

TABLE 2-continued

| Compound No. | Dose g/a | Herbicidal effect | | | |
|---|---|---|---|---|---|
| | | E.C. | R.I. | C.D. | S.J. |
| | 6.25 | 5 | 5 | 5 | 3 |
| 58 | 50 | 5 | 5 | 5 | 5 |
| | 25 | 5 | 5 | 5 | 4 |
| | 12.5 | 5 | 5 | 5 | 4 |
| | 6.25 | 4 | 5 | 5 | 3 |
| 59 | 50 | 5 | 5 | 5 | 5 |
| | 25 | 5 | 5 | 5 | 5 |
| | 12.5 | 4 | 5 | 5 | 4 |
| | 6.25 | 4 | 5 | 5 | 3 |
| 60 | 50 | 5 | 5 | 5 | 5 |
| | 25 | 5 | 5 | 5 | 4 |
| | 12.5 | 4 | 5 | 5 | 4 |
| | 6.25 | 4 | 4 | 5 | 3 |
| 61 | 50 | 5 | 5 | 5 | 4 |
| | 25 | 5 | 5 | 5 | 4 |
| | 12.5 | 5 | 5 | 5 | 4 |
| | 6.25 | 4 | 5 | 5 | 3 |
| 62 | 50 | 5 | 5 | 5 | 5 |
| | 25 | 5 | 5 | 5 | 4 |
| | 12.5 | 5 | 5 | 5 | 4 |
| | 6.25 | 4 | 5 | 5 | 3 |
| 63 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 4 |
| 64 | 50 | 5 | 5 | 5 | 5 |
| | 25 | 5 | 5 | 5 | 5 |
| | 12.5 | 5 | 5 | 5 | 4 |
| | 6.25 | 5 | 5 | 5 | 4 |
| 65 | 50 | 5 | 5 | 5 | 5 |
| | 25 | 5 | 5 | 5 | 4 |
| | 12.5 | 5 | 5 | 5 | 4 |
| | 6.25 | 5 | 5 | 5 | 3 |
| 66 | 50 | 4 | 5 | 5 | 5 |
| | 25 | 4 | 5 | 5 | 5 |
| | 12.5 | 3 | 5 | 5 | 4 |
| | 6.25 | 2 | 4 | 4 | 3 |
| 67 | 50 | 5 | 5 | 5 | 5 |
| | 25 | 5 | 5 | 5 | 4 |
| | 12.5 | 4 | 5 | 5 | 4 |
| | 6.25 | 4 | 5 | 5 | 4 |
| 68 | 50 | 5 | 5 | 5 | 4 |
| | 25 | 4 | 5 | 5 | 4 |
| | 12.5 | 4 | 4 | 5 | 4 |
| | 6.25 | 4 | 4 | 5 | 3 |
| 69 | 50 | 4 | 4 | 5 | 4 |
| | 25 | 3 | 4 | 4 | 4 |
| | 12.5 | 1 | 4 | 4 | 2 |
| | 6.25 | 0 | 3 | 3 | 1 |
| 70 | 50 | 4 | 4 | 5 | 4 |
| | 25 | 2 | 4 | 4 | 1 |
| | 12.5 | 1 | 3 | 4 | 0 |
| | 6.25 | 0 | 3 | 2 | 0 |
| 75 | 50 | 5 | 5 | 5 | 5 |
| | 25 | 5 | 5 | 5 | 5 |
| | 12.5 | 5 | 5 | 5 | 5 |
| | 6.25 | 3 | 4 | 5 | 4 |
| 76 | 50 | 5 | 5 | 5 | 5 |
| | 25 | 5 | 5 | 5 | 5 |
| | 12.5 | 4 | 5 | 5 | 4 |
| | 6.25 | 4 | 4 | 5 | 4 |
| 77 | 50 | 5 | 5 | 5 | 5 |
| | 25 | 5 | 5 | 5 | 5 |
| | 12.5 | 4 | 4 | 5 | 4 |
| | 6.25 | 4 | 4 | 4 | 3 |
| 78 | 50 | 5 | 5 | 5 | 5 |
| | 25 | 5 | 5 | 5 | 4 |
| | 12.5 | 4 | 5 | 5 | 4 |
| | 6.25 | 3 | 4 | 4 | 3 |
| 79 | 50 | 5 | 5 | 5 | 5 |
| | 25 | 4 | 5 | 5 | 4 |
| | 12.5 | 4 | 5 | 5 | 4 |
| | 6.25 | 3 | 4 | 4 | 3 |
| 80 | 50 | 5 | 5 | 5 | 5 |
| | 25 | 5 | 5 | 5 | 5 |
| | 12.5 | 5 | 5 | 5 | 5 |
| | 6.25 | 4 | 5 | 5 | 4 |
| 81 | 50 | 5 | 5 | 5 | 5 |
| | 25 | 5 | 5 | 5 | 5 |
| | 12.5 | 5 | 5 | 5 | 4 |
| | 6.25 | 4 | 5 | 5 | 4 |
| 82 | 50 | 5 | 5 | 5 | 4 |
| | 25 | 4 | 5 | 5 | 4 |
| | 12.5 | 4 | 5 | 5 | 4 |
| | 6.25 | 3 | 5 | 5 | 3 |
| 90 | 50 | 5 | 5 | 5 | 5 |
| | 25 | 5 | 5 | 5 | 5 |
| | 12.5 | 5 | 5 | 5 | 5 |
| | 6.25 | 4 | 4 | 5 | 3 |
| 91 | 50 | 5 | 5 | 5 | 5 |
| | 25 | 5 | 5 | 5 | 5 |
| | 12.5 | 5 | 5 | 5 | 4 |
| | 6.25 | 4 | 5 | 5 | 4 |
| 92 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 4 |
| 93 | 50 | 5 | 5 | 5 | 5 |
| | 25 | 5 | 5 | 5 | 4 |
| | 12.5 | 5 | 5 | 5 | 4 |
| | 6.25 | 4 | 5 | 4 | 3 |
| 94 | 50 | 5 | 5 | 5 | 5 |
| | 25 | 5 | 5 | 5 | 5 |
| | 12.5 | 5 | 5 | 5 | 4 |
| | 6.25 | 4 | 5 | 5 | 3 |
| 95 | 50 | 5 | 5 | 5 | 5 |
| | 25 | 5 | 5 | 5 | 4 |
| | 12.5 | 5 | 5 | 5 | 3 |
| | 6.25 | 5 | 4 | 5 | 3 |
| 96 | 50 | 5 | 5 | 5 | 5 |
| | 25 | 5 | 5 | 5 | 5 |
| | 12.5 | 5 | 5 | 5 | 4 |
| | 6.25 | 4 | 4 | 5 | 4 |
| 97 | 50 | 5 | 5 | 5 | 5 |
| | 25 | 5 | 5 | 5 | 5 |
| | 12.5 | 5 | 5 | 5 | 5 |
| | 6.25 | 4 | 5 | 5 | 4 |
| 98 | 50 | 5 | 5 | 5 | 5 |
| | 25 | 4 | 5 | 5 | 4 |
| | 12.5 | 4 | 4 | 4 | 4 |
| | 6.25 | 3 | 4 | 4 | 3 |
| 99 | 50 | 5 | 5 | 5 | 5 |
| | 25 | 5 | 5 | 5 | 5 |
| | 12.5 | 4 | 4 | 5 | 4 |
| | 6.25 | 4 | 3 | 4 | 3 |
| 100 | 50 | 5 | 4 | 5 | 4 |
| | 25 | 4 | 4 | 4 | 4 |
| | 12.5 | 3 | 4 | 4 | 4 |
| | 6.25 | 3 | 4 | 4 | 3 |
| 101 | 50 | 5 | 5 | 5 | 5 |
| | 25 | 5 | 5 | 4 | 4 |
| | 12.5 | 4 | 4 | 4 | 4 |
| | 6.25 | 3 | 3 | 3 | 3 |
| 102 | 50 | 5 | 5 | 5 | 5 |
| | 25 | 5 | 5 | 5 | 5 |
| | 12.5 | 5 | 5 | 5 | 5 |
| | 6.25 | 4 | 4 | 5 | 4 |
| 103 | 50 | 5 | 5 | 5 | 5 |
| | 25 | 5 | 5 | 5 | 5 |
| | 12.5 | 5 | 5 | 5 | 5 |
| | 6.25 | 4 | 4 | 5 | 4 |
| 104 | 50 | 5 | 5 | 5 | 5 |
| | 25 | 5 | 5 | 5 | 5 |
| | 12.5 | 5 | 5 | 5 | 5 |
| | 6.25 | 5 | 5 | 5 | 4 |
| 105 | 50 | 5 | 5 | 5 | 5 |
| | 25 | 5 | 5 | 5 | 5 |
| | 12.5 | 5 | 5 | 5 | 5 |
| | 6.25 | 4 | 5 | 5 | 4 |
| 106 | 50 | 5 | 5 | 5 | 5 |
| | 25 | 5 | 5 | 5 | 5 |
| | 12.5 | 5 | 5 | 5 | 4 |
| | 6.25 | 5 | 5 | 5 | 4 |
| 107 | 50 | 5 | 5 | 5 | 5 |
| | 25 | 5 | 5 | 5 | 5 |
| | 12.5 | 5 | 5 | 5 | 5 |
| | 6.25 | 4 | 4 | 5 | 4 |
| 108 | 50 | 5 | 5 | 5 | 5 |

TABLE 2-continued

| Compound No. | Dose g/a | Herbicidal effect | | | |
|---|---|---|---|---|---|
| | | E.C. | R.I. | C.D. | S.J. |
| | 25 | 5 | 5 | 5 | 4 |
| | 12.5 | 5 | 5 | 5 | 4 |
| | 6.25 | 5 | 4 | 5 | 4 |
| Agent A | 50 | 5 | 2 | 5 | 1 |
| | 25 | 2 | 0 | 4 | 0 |
| | 12.5 | 0 | 0 | 1 | 0 |
| | 6.25 | 0 | 0 | 0 | 0 |
| Agent C | 50 | 4 | 5 | 5 | 5 |
| | 25 | 3 | 4 | 5 | 4 |
| | 12.5 | 1 | 4 | 5 | 3 |
| | 6.25 | 0 | 1 | 3 | 0 |
| non treatment | — | 0 | 0 | 0 | 0 |

Experimental Example 2

Phytotoxicity Test on Transplanted Young Rice Seedlings

Paddy alluvial clayish loam was charged in each of Wagner pots with an area of 1/5000 are and applied with a fertilizer, followed by adding water and puddling and levelling. Thereafter, waterfield rice seedlings of the 2.1 stage (variety: Koshihikari, plant length: about 10 cm, quality of seedling: good) were used and two batch, each consisting of two seedlings, were shallowly planted in each pot at a depth of about 1 cm. The depth of water was held at 3.5 cm. The granulars containing the compounds in Table below as an effective component obtained in Preparation Example 2 were each applied at the day of the transplantation and at the seventh day after the transplantation by dropping into the submerged field in amounts of 100, 50, 25 and 12.5 g per are as an effective component.

After the treatment with the agents, seepage was effected for 2 days at a rate of 3 cm/day and then the seedlings were cultivated and managed in a greenhouse. The phytotoxicity was checked at the 21st day after the chemical treatment with the results shown in Table 3.

The degree of the phytotoxicity was evaluated according to the following standard of judgement.

| Grade | Degree of Injury |
|---|---|
| 0 | no injury |
| 1 | slight injury |
| 2 | moderate injury |
| 3 | fair injury |
| 4 | considerable injury |
| 5 | withered |

TABLE 3

| Compound No. | Dose g/a | Phytotoxicity | |
|---|---|---|---|
| | | same day transplantation | 7 days after transplantation |
| 1 | 100 | 0 | 0 |
| | 50 | 0 | 0 |
| | 25 | 0 | 0 |
| | 12.5 | 0 | 0 |
| 2 | 100 | 1 | 0 |
| | 50 | 0 | 0 |
| | 25 | 0 | 0 |
| | 12.5 | 0 | 0 |
| 3 | 100 | 0 | 0 |
| | 50 | 0 | 0 |
| | 25 | 0 | 0 |
| | 12.5 | 0 | 0 |
| 4 | 100 | 0 | 0 |
| | 50 | 0 | 0 |
| | 25 | 0 | 0 |
| | 12.5 | 0 | 0 |
| 5 | 100 | 1 | 0 |
| | 50 | 0 | 0 |
| | 25 | 0 | 0 |
| | 12.5 | 0 | 0 |
| 6 | 100 | 1 | 0 |
| | 50 | 0 | 0 |
| | 25 | 0 | 0 |
| | 12.5 | 0 | 0 |
| 7 | 100 | 2 | 1 |
| | 50 | 0 | 0 |
| | 25 | 0 | 0 |
| | 12.5 | 0 | 0 |
| 8 | 100 | 1 | 0 |
| | 50 | 0 | 0 |
| | 25 | 0 | 0 |
| | 12.5 | 0 | 0 |
| 9 | 100 | 2 | 0 |
| | 50 | 0 | 0 |
| | 25 | 0 | 0 |
| | 12.5 | 0 | 0 |
| 10 | 100 | 1 | 1 |
| | 50 | 0 | 0 |
| | 25 | 0 | 0 |
| | 12.5 | 0 | 0 |
| 11 | 100 | 0 | 0 |
| | 50 | 0 | 0 |
| | 25 | 0 | 0 |
| | 12.5 | 0 | 0 |
| 12 | 100 | 1 | 0 |
| | 50 | 0 | 0 |
| | 25 | 0 | 0 |
| | 12.5 | 0 | 0 |
| 13 | 100 | 1 | 0 |
| | 50 | 0 | 0 |
| | 25 | 0 | 0 |
| | 12.5 | 0 | 0 |
| 14 | 100 | 1 | 0 |
| | 50 | 0 | 0 |
| | 25 | 0 | 0 |
| | 12.5 | 0 | 0 |
| 15 | 100 | 1 | 1 |
| | 50 | 0 | 0 |
| | 25 | 0 | 0 |
| | 12.5 | 0 | 0 |
| 16 | 100 | 0 | 0 |
| | 50 | 0 | 0 |
| | 25 | 0 | 0 |
| | 12.5 | 0 | 0 |
| 17 | 100 | 0 | 0 |
| | 50 | 0 | 0 |
| | 25 | 0 | 0 |
| | 12.5 | 0 | 0 |
| 18 | 100 | 0 | 0 |
| | 50 | 0 | 0 |
| | 25 | 0 | 0 |
| | 12.5 | 0 | 0 |
| 19 | 100 | 0 | 0 |
| | 50 | 0 | 0 |
| | 25 | 0 | 0 |
| | 12.5 | 0 | 0 |
| 20 | 100 | 0 | 0 |
| | 50 | 0 | 0 |
| | 25 | 0 | 0 |
| | 12.5 | 0 | 0 |
| 21 | 100 | 0 | 0 |
| | 50 | 0 | 0 |
| | 25 | 0 | 0 |
| | 12.5 | 0 | 0 |
| 22 | 100 | 0 | 0 |
| | 50 | 0 | 0 |
| | 25 | 0 | 0 |
| | 12.5 | 0 | 0 |
| 23 | 100 | 0 | 0 |
| | 50 | 0 | 0 |
| | 25 | 0 | 0 |
| | 12.5 | 0 | 0 |

TABLE 3-continued

| Compound No. | Dose g/a | Phytotoxicity same day transplantation | 7 days after transplantation |
|---|---|---|---|
| 24 | 100 | 0 | 0 |
|  | 50 | 0 | 0 |
|  | 25 | 0 | 0 |
|  | 12.5 | 0 | 0 |
| 25 | 100 | 3 | 1 |
|  | 50 | 1 | 0 |
|  | 25 | 0 | 0 |
|  | 12.5 | 0 | 0 |
| 26 | 100 | 1 | 0 |
|  | 50 | 0 | 0 |
|  | 25 | 0 | 0 |
|  | 12.5 | 0 | 0 |
| 27 | 100 | 1 | 0 |
|  | 50 | 0 | 0 |
|  | 25 | 0 | 0 |
|  | 12.5 | 0 | 0 |
| 28 | 100 | 2 | 1 |
|  | 50 | 0 | 0 |
|  | 25 | 0 | 0 |
|  | 12.5 | 0 | 0 |
| 29 | 100 | 0 | 0 |
|  | 50 | 0 | 0 |
|  | 25 | 0 | 0 |
|  | 12.5 | 0 | 0 |
| 30 | 100 | 0 | 0 |
|  | 50 | 0 | 0 |
|  | 25 | 0 | 0 |
|  | 12.5 | 0 | 0 |
| 85 | 100 | 0 | 0 |
|  | 50 | 0 | 0 |
|  | 25 | 0 | 0 |
|  | 12.5 | 0 | 0 |
| 86 | 100 | 0 | 0 |
|  | 50 | 0 | 0 |
|  | 25 | 0 | 0 |
|  | 12.5 | 0 | 0 |
| 87 | 100 | 0 | 0 |
|  | 50 | 0 | 0 |
|  | 25 | 0 | 0 |
|  | 12.5 | 0 | 0 |
| 88 | 100 | 0 | 0 |
|  | 50 | 0 | 0 |
|  | 25 | 0 | 0 |
|  | 12.5 | 0 | 0 |
| 89 | 100 | 0 | 0 |
|  | 50 | 0 | 0 |
|  | 25 | 0 | 0 |
|  | 12.5 | 0 | 0 |
| 90 | 100 | 0 | 0 |
|  | 50 | 0 | 0 |
|  | 25 | 0 | 0 |
|  | 12.5 | 0 | 0 |
| 91 | 100 | 1 | 0 |
|  | 50 | 0 | 0 |
|  | 25 | 0 | 0 |
|  | 12.5 | 0 | 0 |
| 92 | 100 | 1 | 1 |
|  | 50 | 0 | 0 |
|  | 25 | 0 | 0 |
|  | 12.5 | 0 | 0 |
| 93 | 100 | 1 | 0 |
|  | 50 | 0 | 0 |
|  | 25 | 0 | 0 |
|  | 12.5 | 0 | 0 |
| 94 | 100 | 0 | 0 |
|  | 50 | 0 | 0 |
|  | 25 | 0 | 0 |
|  | 12.5 | 0 | 0 |
| 95 | 100 | 0 | 0 |
|  | 50 | 0 | 0 |
|  | 25 | 0 | 0 |
|  | 12.5 | 0 | 0 |
| 96 | 100 | 0 | 0 |
|  | 50 | 0 | 0 |
|  | 25 | 0 | 0 |
|  | 12.5 | 0 | 0 |
| 97 | 100 | 0 | 0 |
|  | 50 | 0 | 0 |
|  | 25 | 0 | 0 |
|  | 12.5 | 0 | 0 |
| 98 | 100 | 0 | 0 |
|  | 50 | 0 | 0 |
|  | 25 | 0 | 0 |
|  | 12.5 | 0 | 0 |
| 99 | 100 | 0 | 0 |
|  | 50 | 0 | 0 |
|  | 25 | 0 | 0 |
|  | 12.5 | 0 | 0 |
| 100 | 100 | 0 | 0 |
|  | 50 | 0 | 0 |
|  | 25 | 0 | 0 |
|  | 12.5 | 0 | 0 |
| 101 | 100 | 0 | 0 |
|  | 50 | 0 | 0 |
|  | 25 | 0 | 0 |
|  | 12.5 | 0 | 0 |
| 102 | 100 | 0 | 0 |
|  | 50 | 0 | 0 |
|  | 25 | 0 | 0 |
|  | 12.5 | 0 | 0 |
| 103 | 100 | 0 | 0 |
|  | 50 | 0 | 0 |
|  | 25 | 0 | 0 |
|  | 12.5 | 0 | 0 |
| 104 | 100 | 0 | 0 |
|  | 50 | 0 | 0 |
|  | 25 | 0 | 0 |
|  | 12.5 | 0 | 0 |
| 105 | 100 | 0 | 0 |
|  | 50 | 0 | 0 |
|  | 25 | 0 | 0 |
|  | 12.5 | 0 | 0 |
| 106 | 100 | 0 | 0 |
|  | 50 | 0 | 0 |
|  | 25 | 0 | 0 |
|  | 12.5 | 0 | 0 |
| 107 | 100 | 0 | 0 |
|  | 50 | 0 | 0 |
|  | 25 | 0 | 0 |
|  | 12.5 | 0 | 0 |
| 108 | 100 | 0 | 0 |
|  | 50 | 0 | 0 |
|  | 25 | 0 | 0 |
|  | 12.5 | 0 | 0 |
| 109 | 100 | 0 | 0 |
|  | 50 | 0 | 0 |
|  | 25 | 0 | 0 |
|  | 12.5 | 0 | 0 |
| 110 | 100 | 0 | 0 |
|  | 50 | 0 | 0 |
|  | 25 | 0 | 0 |
|  | 12.5 | 0 | 0 |
| 111 | 100 | 0 | 0 |
|  | 50 | 0 | 0 |
|  | 25 | 0 | 0 |
|  | 12.5 | 0 | 0 |
| 112 | 100 | 0 | 0 |
|  | 50 | 0 | 0 |
|  | 25 | 0 | 0 |
|  | 12.5 | 0 | 0 |
| 113 | 100 | 0 | 0 |
|  | 50 | 0 | 0 |
|  | 25 | 0 | 0 |
|  | 12.5 | 0 | 0 |
| 114 | 100 | 0 | 0 |
|  | 50 | 0 | 0 |
|  | 25 | 0 | 0 |
|  | 12.5 | 0 | 0 |
| 115 | 100 | 0 | 0 |
|  | 50 | 0 | 0 |
|  | 25 | 0 | 0 |
|  | 12.5 | 0 | 0 |
| 116 | 100 | 0 | 0 |
|  | 50 | 0 | 0 |
|  | 25 | 0 | 0 |
|  | 12.5 | 0 | 0 |

TABLE 3-continued

| Compound No. | Dose g/a | Phytotoxicity same day transplantation | 7 days after transplantation |
|---|---|---|---|
| 117 | 100 | 0 | 0 |
| | 50 | 0 | 0 |
| | 25 | 0 | 0 |
| | 12.5 | 0 | 0 |
| 118 | 100 | 0 | 0 |
| | 50 | 0 | 0 |
| | 25 | 0 | 0 |
| | 12.5 | 0 | 0 |
| 119 | 100 | 0 | 0 |
| | 50 | 0 | 0 |
| | 25 | 0 | 0 |
| | 12.5 | 0 | 0 |
| 120 | 100 | 0 | 0 |
| | 50 | 0 | 0 |
| | 25 | 0 | 0 |
| | 12.5 | 0 | 0 |
| Agent B | 100 | 3 | 2 |
| | 50 | 2 | 0 |
| | 25 | 1 | 0 |
| | 12.5 | 0 | 0 |
| Agent C | 100 | 5 | 4 |
| | 50 | 5 | 4 |
| | 25 | 4 | 1 |
| | 12.5 | 2 | 0 |
| non treatment | — | 0 | 0 |

Experimental Example 3

Phytotoxicity Test on Rice Plants of Germination Stage

Paddy alluvial clayish loam was filled in each of ceramic pots with an area of 1/8850 are and applied with a fertilizer, followed by adding water thereto and puddling and levelling. Seeds of weeds including barnyardgrass, smallflower umbrellaplant, hardstem bulrush, ducktongue weed and hat sedge were uniformly incorporated in the surface layer of the soil. The submerged condition of about 2 cm in depth was kept. At the time of the germination of the weeds, 5 rice seeds (variety: Nihonbare) at the stage of germination were transplanted in each pot. The wettable powders containing the compounds indicated in Table below obtained in Preparation Example 1 were applied by dropping them into the submerged pots in amounts of 100, 50, 25 and 12.5 g per are.

Thereafter, the pots were placed in a greenhouse and the herbicidal effect and the phytotoxicity were checked at the 21st day after the chemical treatment. The results are shown in Table 4 below.

The herbicidal effect was evaluated in the same manner as in Experimental Example 1 and the phytotoxicity was also evaluated as in Experimental Example 2.

TABLE 4

| Compound No. | Dose g/a | Phytotoxicity | Herbicidal effect E.C. | C.D. | S.J. | M.V. | R.I. |
|---|---|---|---|---|---|---|---|
| 67 | 100 | 1 | 5 | 5 | 5 | 5 | 5 |
| | 50 | 0 | 5 | 5 | 5 | 5 | 5 |
| | 25 | 0 | 5 | 5 | 2 | 5 | 5 |
| | 12.5 | 0 | 5 | 5 | 2 | 4 | 5 |
| 68 | 100 | 0 | 5 | 5 | 4 | 5 | 5 |
| | 50 | 0 | 5 | 5 | 3 | 5 | 5 |
| | 25 | 0 | 5 | 5 | 2 | 5 | 5 |
| | 12.5 | 0 | 4 | 5 | 0 | 4 | 4 |
| 69 | 100 | 0 | 4 | 5 | 3 | 3 | 3 |
| | 50 | 0 | 4 | 5 | 3 | 1 | 3 |
| | 25 | 0 | 3 | 4 | 1 | 1 | 3 |
| | 12.5 | 0 | 3 | 4 | 1 | 0 | 2 |
| 70 | 100 | 0 | 4 | 4 | 4 | 4 | 4 |
| | 50 | 0 | 4 | 4 | 2 | 3 | 3 |
| | 25 | 0 | 3 | 3 | 1 | 1 | 3 |
| | 12.5 | 0 | 2 | 3 | 0 | 0 | 2 |
| 93 | 100 | 1 | 5 | 5 | 5 | 5 | 5 |
| | 50 | 0 | 5 | 5 | 5 | 5 | 5 |
| | 25 | 0 | 5 | 3 | 5 | 5 | 5 |
| | 12.5 | 0 | 5 | 4 | 2 | 4 | 4 |
| 94 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 4 | 0 | 4 | 4 |
| 95 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 4 | 1 | 4 | 5 |
| 102 | 100 | 2 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 5 | 5 | 5 |
| 103 | 100 | 0 | 5 | 5 | 5 | 5 | 5 |
| | 50 | 0 | 5 | 5 | 4 | 5 | 5 |
| | 25 | 0 | 5 | 5 | 3 | 5 | 5 |
| | 12.5 | 0 | 5 | 5 | 3 | 4 | 5 |
| 104 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 5 | 5 | 5 |
| 105 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 3 | 5 | 5 |
| 106 | 100 | 2 | 5 | 5 | 5 | 5 | 5 |
| | 50 | 1 | 5 | 5 | 5 | 5 | 5 |
| | 25 | 0 | 5 | 5 | 5 | 5 | 5 |
| | 12.5 | 0 | 5 | 5 | 2 | 5 | 5 |
| 107 | 100 | 0 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 4 | 2 | 4 | 5 |
| 108 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 2 | 5 | 5 |
| 116 | 100 | 0 | 5 | 5 | 4 | 5 | 5 |
| | 50 | 0 | 5 | 5 | 4 | 5 | 4 |
| | 25 | 0 | 4 | 5 | 1 | 4 | 4 |
| | 12.5 | 0 | 3 | 4 | 0 | 3 | 3 |
| 117 | 100 | 0 | 4 | 5 | 4 | 5 | 5 |
| | 50 | 0 | 4 | 4 | 4 | 4 | 4 |
| | 25 | 0 | 3 | 4 | 0 | 3 | 3 |
| | 12.5 | 0 | 3 | 3 | 0 | 3 | 1 |
| 121 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 5 | 5 | 5 |
| 122 | 100 | 2 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 5 | 5 | 5 |
| 123 | 100 | 0 | 5 | 5 | 5 | 5 | 5 |
| | 50 | 0 | 5 | 5 | 5 | 5 | 5 |
| | 25 | 0 | 5 | 5 | 3 | 5 | 5 |
| | 12.5 | 0 | 5 | 5 | 2 | 5 | 5 |
| 124 | 100 | 0 | 5 | 5 | 4 | 5 | 5 |
| | 50 | 0 | 5 | 5 | 3 | 5 | 5 |
| | 25 | 0 | 5 | 5 | 1 | 5 | 5 |
| | 12.5 | 0 | 5 | 5 | 1 | 4 | 5 |
| 125 | 100 | 0 | 5 | 5 | 5 | 5 | 5 |
| | 50 | 0 | 5 | 5 | 5 | 5 | 5 |
| | 25 | 0 | 5 | 5 | 3 | 5 | 5 |
| | 12.5 | 0 | 5 | 5 | 0 | 5 | 5 |
| 126 | 100 | 0 | 5 | 5 | 5 | 5 | 5 |
| | 50 | 0 | 5 | 5 | 4 | 5 | 5 |
| | 25 | 0 | 5 | 5 | 3 | 5 | 5 |
| | 12.5 | 0 | 3 | 5 | 2 | 5 | 5 |
| 127 | 100 | 0 | 5 | 5 | 5 | 5 | 5 |
| | 50 | 0 | 5 | 5 | 5 | 5 | 5 |
| | 25 | 0 | 5 | 5 | 3 | 5 | 5 |
| | 12.5 | 0 | 4 | 5 | 3 | 5 | 5 |
| 128 | 100 | 0 | 5 | 5 | 5 | 5 | 5 |
| | 50 | 0 | 5 | 5 | 5 | 5 | 5 |
| | 25 | 0 | 5 | 5 | 3 | 5 | 5 |

TABLE 4-continued

| Compound No. | Dose g/a | Phytotoxicity | E.C. | C.D. | S.J. | M.J. | R.I. |
|---|---|---|---|---|---|---|---|
| | 12.5 | 0 | 5 | 5 | 4 | 5 | 5 |
| 129 | 100 | 0 | 5 | 5 | 5 | 5 | 5 |
| | 50 | 0 | 5 | 5 | 4 | 5 | 5 |
| | 25 | 0 | 5 | 5 | 3 | 5 | 5 |
| | 12.5 | 0 | 5 | 4 | 1 | 5 | 5 |
| 130 | 100 | 0 | 5 | 5 | 5 | 5 | 5 |
| | 50 | 0 | 5 | 5 | 5 | 5 | 5 |
| | 25 | 0 | 5 | 5 | 3 | 4 | 5 |
| | 12.5 | 0 | 5 | 5 | 3 | 4 | 3 |
| 131 | 100 | 0 | 5 | 4 | 3 | 5 | 5 |
| | 50 | 0 | 3 | 4 | 1 | 5 | 5 |
| | 25 | 0 | 2 | 2 | 1 | 3 | 4 |
| | 12.5 | 0 | 2 | 1 | 0 | 3 | 3 |
| 132 | 100 | 0 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 2 | 5 | 5 |
| 133 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 3.5 | 5 | 5 |
| 134 | 100 | 0 | 5 | 5 | 5 | 5 | 5 |
| | 50 | 0 | 5 | 5 | 4 | 5 | 5 |
| | 25 | 0 | 5 | 5 | 2 | 5 | 5 |
| | 12.5 | 0 | 5 | 5 | 0 | 4 | 5 |
| 135 | 100 | 0 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 3 | 5 | 5 |
| 136 | 100 | 0 | 5 | 5 | 5 | 5 | 5 |
| | 50 | 0 | 5 | 5 | 4 | 5 | 5 |
| | 25 | 0 | 5 | 5 | 3 | 5 | 5 |
| | 12.5 | 0 | 5 | 5 | 3 | 5 | 5 |
| 137 | 100 | 0 | 5 | 5 | 5 | 5 | 5 |
| | 50 | 0 | 5 | 5 | 5 | 5 | 5 |
| | 25 | 0 | 5 | 5 | 3 | 5 | 4 |
| | 12.5 | 0 | 5 | 5 | 4 | 4 | 5 |
| 138 | 100 | 0 | 5 | 5 | 4 | 5 | 5 |
| | 50 | 0 | 5 | 5 | 3 | 5 | 5 |
| | 25 | 0 | 5 | 5 | 0 | 5 | 5 |
| | 12.5 | 0 | 5 | 5 | 0 | 5 | 5 |
| 139 | 100 | 1 | 5 | 5 | 5 | 5 | 5 |
| | 50 | 0 | 5 | 5 | 5 | 5 | 5 |
| | 25 | 0 | 4.5 | 5 | 5 | 5 | 4.5 |
| | 12.5 | 0 | 4 | 5 | 5 | 4.5 | 4 |
| 140 | 100 | 1 | 5 | 5 | 5 | 5 | 5 |
| | 50 | 0 | 5 | 5 | 5 | 5 | 5 |
| | 25 | 0 | 5 | 5 | 5 | 5 | 5 |
| | 12.5 | 0 | 5 | 5 | 2.5 | 4 | 4.5 |
| 141 | 100 | 1 | 5 | 5 | 5 | 5 | 5 |
| | 50 | 0 | 5 | 5 | 5 | 5 | 5 |
| | 25 | 0 | 5 | 5 | 4.5 | 5 | 5 |
| | 12.5 | 0 | 4 | 4.5 | 3.5 | 5 | 4.5 |
| 142 | 100 | 0 | 5 | 5 | 5 | 5 | 5 |
| | 50 | 0 | 1 | 5 | 5 | 5 | 5 |
| | 25 | 0 | 0 | 5 | 2 | 5 | 5 |
| | 12.5 | 0 | 0 | 5 | 0 | 5 | 5 |
| 143 | 100 | 0 | 5 | 5 | 5 | 5 | 5 |
| | 50 | 0 | 5 | 5 | 5 | 5 | 5 |
| | 25 | 0 | 4.5 | 5 | 4.5 | 5 | 5 |
| | 12.5 | 0 | 3 | 4.5 | 4.5 | 4 | 4.5 |
| 144 | 100 | 0 | 5 | 4 | 5 | 5 | 5 |
| | 50 | 0 | 4 | 2 | 3 | 4 | 5 |
| | 25 | 0 | 4 | 2 | 1 | 4 | 5 |
| | 12.5 | 0 | 4 | 1 | 0 | 3 | 3 |
| 145 | 100 | 1 | 5 | 5 | — | 5 | 5 |
| | 50 | 0 | 5 | 5 | — | 5 | 5 |
| | 25 | 0 | 4 | 5 | — | 5 | 5 |
| | 12.5 | 0 | 4 | 4 | — | 4 | 5 |
| 146 | 100 | 0 | 5 | 5 | — | 5 | 5 |
| | 50 | 0 | 5 | 5 | — | 5 | 5 |
| | 25 | 0 | 3.5 | 5 | — | 4 | 5 |
| | 12.5 | 0 | 2.5 | 4 | — | 4 | 5 |
| 147 | 100 | 0 | 5 | 5 | 5 | 5 | 5 |
| | 50 | 0 | 5 | 5 | 3 | 4 | 5 |
| | 25 | 0 | 4 | 5 | 3 | 4 | 4 |
| | 12.5 | 0 | 3 | 4.5 | 2.5 | 1 | 3 |
| 148 | 100 | 0 | 5 | 4 | 4 | 4 | 5 |
| | 50 | 0 | 4 | 4 | 3 | 4 | 4 |
| | 25 | 0 | 3 | 3 | 1 | 1 | 2 |
| | 12.5 | 0 | 2.5 | 1 | 0 | 0 | 2 |
| 149 | 100 | 0 | 3 | 3 | 3 | 3 | 4 |
| | 50 | 0 | 2 | 3 | 1 | 0 | 2 |
| | 25 | 0 | 0 | 0 | 0 | 0 | 0 |
| | 12.5 | 0 | 0 | 0 | 0 | 0 | 0 |

| Compound No. | Dose g/a | Phytotoxicity | E.C. | C.D. | S.J. | M.J. | R.I. |
|---|---|---|---|---|---|---|---|
| 150 | 100 | 0 | 4 | 3 | 3 | 3 | 4 |
| | 50 | 0 | 3 | 2 | 2 | 2 | 3 |
| | 25 | 0 | 1 | 0 | 2 | 0 | 2 |
| | 12.5 | 0 | 0 | 0 | 0 | 0 | 0 |
| 151 | 100 | 1 | 5 | 5 | 5 | 5 | 5 |
| | 50 | 0 | 5 | 5 | 5 | 5 | 5 |
| | 25 | 0 | 5 | 5 | 4.5 | 5 | 5 |
| | 12.5 | 0 | 4.5 | 5 | 3.5 | 5 | 5 |
| 152 | 100 | 0 | 5 | 5 | — | 5 | 5 |
| | 50 | 0 | 5 | 5 | — | 5 | 5 |
| | 25 | 0 | 5 | 5 | — | 5 | 5 |
| | 12.5 | 0 | 5 | 5 | — | 5 | 5 |
| 153 | 100 | 0 | 5 | 5 | 5 | 5 | 5 |
| | 50 | 0 | 5 | 5 | 5 | 5 | 5 |
| | 25 | 0 | 5 | 5 | 4.5 | 5 | 5 |
| | 12.5 | 0 | 4 | 5 | 5 | 5 | 5 |
| 154 | 100 | 1 | 5 | 5 | 5 | 5 | 5 |
| | 50 | 0 | 5 | 5 | 3 | 5 | 5 |
| | 25 | 0 | 5 | 5 | 1 | 5 | 5 |
| | 12.5 | 0 | 5 | 5 | 0 | 5 | 5 |
| 155 | 100 | 0 | 5 | 5 | 5 | 5 | 5 |
| | 50 | 0 | 5 | 5 | 4 | 5 | 5 |
| | 25 | 0 | 5 | 5 | 3 | 5 | 5 |
| | 12.5 | 0 | 4 | 5 | 3 | 5 | 5 |

| Compound No. | Dose g/a | Phytotoxicity | E.C. | C.D. | S.J. | M.V. | R.I. |
|---|---|---|---|---|---|---|---|
| 156 | 100 | 0 | 5 | 5 | 5 | 5 | 5 |
| | 50 | 0 | 5 | 5 | 2 | 5 | 5 |
| | 25 | 0 | 4 | 5 | 1 | 5 | 5 |
| | 12.5 | 0 | 2.5 | 5 | 1 | 5 | 5 |
| 157 | 100 | 0 | 5 | 5 | 5 | 5 | 5 |
| | 50 | 0 | 5 | 5 | 4 | 5 | 5 |
| | 25 | 0 | 3.5 | 5 | 4 | 5 | 5 |
| | 12.5 | 0 | 3 | 5 | 3 | 5 | 5 |
| 158 | 100 | 0 | 5 | 5 | — | 5 | 5 |
| | 50 | 0 | 5 | 5 | — | 5 | 5 |
| | 25 | 0 | 5 | 4 | — | 5 | 5 |
| | 12.5 | 0 | 4 | 3.5 | — | 5 | 4 |
| 159 | 100 | 1 | 5 | 5 | — | 5 | 5 |
| | 50 | 0 | 5 | 4.5 | — | 5 | 5 |
| | 25 | 0 | 5 | 4 | — | 4 | 5 |
| | 12.5 | 0 | 5 | 4 | — | 4 | 5 |
| 160 | 100 | 0 | 5 | 5 | — | 5 | 5 |
| | 50 | 0 | 5 | 5 | — | 4 | 5 |
| | 25 | 0 | 5 | 5 | — | 4 | 4.5 |
| | 12.5 | 0 | 4 | 5 | — | 3 | 4.5 |
| 161 | 100 | 1 | 5 | 5 | — | 5 | 5 |
| | 50 | 0 | 5 | 5 | — | 5 | 5 |
| | 25 | 0 | 5 | 5 | — | 5 | 5 |
| | 12.5 | 0 | 5 | 5 | — | 5 | 5 |
| 162 | 100 | 1 | 5 | 5 | — | 5 | 5 |
| | 50 | 0 | 5 | 5 | — | 5 | 5 |
| | 25 | 0 | 5 | 5 | — | 5 | 5 |
| | 12.5 | 0 | 5 | 4 | — | 5 | 4 |
| 163 | 100 | 1 | 5 | 5 | — | 5 | 5 |
| | 50 | 0 | 5 | 5 | — | 5 | 5 |
| | 25 | 0 | 5 | 5 | — | 5 | 5 |
| | 12.5 | 0 | 5 | 5 | — | 5 | 5 |
| 164 | 100 | 0 | 5 | 5 | — | 5 | 5 |
| | 50 | 0 | 5 | 5 | — | 5 | 5 |
| | 25 | 0 | 5 | 5 | — | 5 | 5 |
| | 12.5 | 0 | 5 | 5 | — | 5 | 5 |
| 165 | 100 | 0 | 5 | 5 | — | 5 | 5 |
| | 50 | 0 | 4 | 3 | — | 5 | 5 |
| | 25 | 0 | 4 | 3 | — | 4 | 5 |
| | 12.5 | 0 | 3.5 | 3 | — | 4 | 5 |
| 166 | 100 | 0 | 5 | 5 | — | 5 | 5 |
| | 50 | 0 | 4 | 5 | — | 4 | 5 |
| | 25 | 0 | 4 | 5 | — | 4 | 5 |
| | 12.5 | 0 | 4 | 4 | — | 3 | 5 |
| 167 | 100 | 0 | 5 | 5 | — | 5 | 5 |
| | 50 | 0 | 5 | 5 | — | 5 | 5 |
| | 25 | 0 | 5 | 5 | — | 5 | 5 |

TABLE 4-continued

| | | | | | | | | | | | | | | |
|---|---|---|---|---|---|---|---|---|---|---|---|---|---|---|
| | 12.5 | 0 | 5 | 5 | — | 5 | 5 | | | 50 | 0 | 4.5 | 5 | 5 | 5 | 5 |
| 168 | 100 | 0 | 5 | 5 | — | 5 | 5 | | | 25 | 0 | 4.5 | 5 | 4 | 4.5 | 5 |
| | 50 | 0 | 5 | 5 | — | 5 | 5 | | | 12.5 | 0 | 4.5 | 5 | 1 | 4.5 | 5 |
| | 25 | 0 | 5 | 5 | — | 5 | 5 | | 189 | 100 | 0 | 5 | 5 | 5 | 5 | 5 |
| | 12.5 | 0 | 5 | 5 | — | 5 | 4 | | | 50 | 0 | 5 | 5 | 4 | 5 | 5 |
| 169 | 100 | 0 | 5 | 5 | — | 5 | 5 | | | 25 | 0 | 5 | 5 | 2.5 | 5 | 5 |
| | 50 | 0 | 5 | 4.5 | — | 4 | 5 | | | 12.5 | 0 | 5 | 5 | 1 | 5 | 5 |
| | 25 | 0 | 5 | 5 | — | 3 | 4 | | 190 | 100 | 0 | 5 | 5 | 5 | 5 | 5 |
| | 12.5 | 0 | 5 | 3 | — | 1 | 2 | | | 50 | 0 | 5 | 5 | 3 | 5 | 5 |
| 170 | 100 | 0 | 5 | 5 | — | 5 | 5 | | | 25 | 0 | 5 | 5 | 2 | 5 | 4.5 |
| | 50 | 0 | 5 | 5 | — | 5 | 5 | | | 12.5 | 0 | 4.5 | 5 | 0.5 | 4.5 | 5 |
| | 25 | 0 | 5 | 5 | — | 5 | 5 | | 191 | 100 | 0 | 5 | 5 | 5 | 5 | 5 |
| | 12.5 | 0 | 5 | 4 | — | 5 | 5 | | | 50 | 0 | 5 | 5 | 5 | 5 | 5 |
| 171 | 100 | 0 | 5 | 5 | — | 5 | 5 | | | 25 | 0 | 5 | 5 | 5 | 5 | 5 |
| | 50 | 0 | 5 | 5 | — | 5 | 4 | | | 12.5 | 0 | 4.5 | 5 | 1.5 | 4.5 | 5 |
| | 25 | 0 | 5 | 5 | — | 3 | 4 | | 192 | 100 | 0 | 5 | 5 | 5 | 5 | 5 |
| | 12.5 | 0 | 4.5 | 5 | — | 2 | 4 | | | 50 | 0 | 5 | 5 | 5 | 5 | 5 |
| 172 | 100 | 0 | 5 | 5 | 5 | 5 | 5 | | | 25 | 0 | 4.5 | 5 | 4 | 5 | 5 |
| | 50 | 0 | 5 | 5 | 5 | 5 | 5 | | | 12.5 | 0 | 4 | 5 | 3 | 5 | 5 |
| | 25 | 0 | 5 | 5 | 4 | 5 | 5 | | 193 | 100 | 0 | 5 | 5 | 5 | 5 | 5 |
| | 12.5 | 0 | 4 | 5 | 2.5 | 5 | 5 | | | 50 | 0 | 5 | 5 | 5 | 5 | 5 |
| 173 | 100 | 0 | 5 | 5 | 5 | 5 | 5 | | | 25 | 0 | 4.5 | 5 | 4.5 | 5 | 4 |
| | 50 | 0 | 5 | 5 | 4 | 5 | 5 | | | 12.5 | 0 | 4.5 | 5 | 4 | 5 | 5 |
| | 25 | 0 | 4.5 | 5 | 3.5 | 4 | 5 | | 194 | 100 | 0 | 5 | 5 | 5 | 5 | 5 |
| | 12.5 | 0 | 3.5 | 5 | 3 | 4 | 5 | | | 50 | 0 | 5 | 5 | 5 | 5 | 5 |
| 174 | 100 | 0 | 5 | 5 | 5 | 5 | 5 | | | 25 | 0 | 4.5 | 4.5 | 5 | 5 | 5 |
| | 50 | 0 | 5 | 5 | 4 | 4 | 5 | | | 12.5 | 0 | 4 | 2.5 | 4 | 5 | 4.5 |
| | 25 | 0 | 4.5 | 5 | 3 | 3 | 5 | | 195 | 100 | 0 | 5 | 5 | 5 | 5 | 5 |
| | 12.5 | 0 | 5 | 5 | 3 | 1 | 5 | | | 50 | 0 | 5 | 5 | 4 | 5 | 5 |
| 175 | 100 | 0 | 5 | 5 | 4 | 5 | 5 | | | 25 | 0 | 4.5 5 | 3.5 | 5 | 4.5 | |
| | 50 | 0 | 5 | 5 | 3 | 5 | 5 | | | 12.5 | 0 | 4.5 | 5 | 4 | 4.5 | 5 |
| | 25 | 0 | 4.5 | 5 | 2 | 4 | 5 | | 196 | 100 | 0 | 5 | 5 | 5 | 5 | 5 |
| | 12.5 | 0 | 4.5 | 5 | 2 | 4 | 5 | | | 50 | 0 | 5 | 5 | 5 | 5 | 5 |
| 176 | 100 | 0 | 5 | 5 | 5 | 5 | 5 | | | 25 | 0 | 4.5 | 5 | 4.5 | 4.5 | 5 |
| | 50 | 0 | 5 | 5 | 4 | 5 | 5 | | | 12.5 | 0 | 4 | 5 | 4.5 | 4 | 5 |
| | 25 | 0 | 5 | 5 | 3.5 | 5 | 5 | | 197 | 100 | 0 | 5 | 5 | 5 | 5 | 5 |
| | 12.5 | 0 | 4 | 5 | 2 | 4 | 5 | | | 50 | 0 | 5 | 5 | 5 | 5 | 5 |
| 177 | 100 | 0 | 5 | 5 | 3 | 5 | 5 | | | 25 | 0 | 4.5 | 5 | 4 | 5 | 5 |
| | 50 | 0 | 5 | 5 | 2 | 5 | 5 | | | 12.5 | 0 | 4 | 5 | 5 | 5 | 5 |
| | 25 | 0 | 4 | 5 | 1.5 | 4 | 5 | | 198 | 100 | 0 | 5 | 5 | 5 | 5 | 5 |
| | 12.5 | 0 | 5 | 5 | 1 | 3.5 | 4.5 | | | 50 | 0 | 5 | 5 | 5 | 5 | 5 |
| 178 | 100 | 0 | 5 | 5 | 5 | 5 | 5 | | | 25 | 0 | 5 | 5 | 5 | 5 | 5 |
| | 50 | 0 | 5 | 5 | 5 | 5 | 5 | | | 12.5 | 0 | 4 | 5 | 4.5 | 5 | 5 |
| | 25 | 0 | 5 | 5 | 4.5 | 5 | 5 | | 199 | 100 | 0 | 5 | 5 | 5 | 5 | 5 |
| | 12.5 | 0 | 5 | 5 | 3 | 5 | 5 | | | 50 | 0 | 5 | 5 | 5 | 5 | 5 |
| 179 | 100 | 0 | 5 | 5 | 5 | 5 | 5 | | | 25 | 0 | 4.5 | 4.5 | 4 | 3 | 5 |
| | 50 | 0 | 5 | 5 | 5 | 5 | 5 | | | 12.5 | 0 | 4 | 5 | 0 | 3 | 1 |
| | 25 | 0 | 5 | 5 | 5 | 5 | 5 | | 200 | 100 | 0 | 5 | 5 | 5 | 5 | 5 |
| | 12.5 | 0 | 5 | 5 | 3.5 | 5 | 5 | | | 50 | 0 | 5 | 5 | 4 | 5 | 5 |
| 180 | 100 | 0 | 5 | 5 | 5 | 5 | 5 | | | 25 | 0 | 4.5 | 4 | 4 | 4.5 | 4.5 |
| | 50 | 0 | 5 | 5 | 5 | 5 | 5 | | | 12.5 | 0 | 3.5 | 4 | 2 | 4 | 5 |
| | 25 | 0 | 5 | 5 | 5 | 5 | 5 | | 201 | 100 | 0 | 5 | 5 | 5 | 5 | 5 |
| | 12.5 | 0 | 5 | 5 | 4.5 | 4.5 | 5 | | | 50 | 0 | 5 | 5 | 5 | 5 | 5 |
| 181 | 100 | 0 | 5 | 5 | 5 | 5 | 5 | | | 25 | 0 | 4 | 5 | 4 | 5 | 5 |
| | 50 | 0 | 5 | 5 | 5 | 5 | 5 | | | 12.5 | 0 | 3.5 | 5 | 3 | 5 | 4.5 |
| | 25 | 0 | 4.5 | 5 | 5 | 5 | 5 | | 202 | 100 | 0 | 5 | 5 | 5 | 5 | 5 |
| | 12.5 | 0 | 4.5 | 5 | 2.5 | 4 | 5 | | | 50 | 0 | 5 | 5 | 4 | 5 | 5 |
| 182 | 100 | 1 | 5 | 5 | 5 | 5 | 5 | | | 25 | 0 | 3.5 | 5 | 3.5 | 5 | 5 |
| | 50 | 0 | 5 | 5 | 5 | 5 | 5 | | | 12.5 | 0 | 3.5 | 4.5 | 4 | 4.5 | 5 |
| | 25 | 0 | 5 | 5 | 3 | 5 | 5 | | 203 | 100 | 1 | 5 | 5 | 5 | 5 | 5 |
| | 12.5 | 0 | 5 | 5 | 5 | 5 | 5 | | | 50 | 0 | 5 | 5 | 5 | 5 | 5 |
| 183 | 100 | 0 | 5 | 5 | 4 | 5 | 5 | | | 25 | 0 | 5 | 5 | 5 | 4 | 5 |
| | 50 | 0 | 4 | 5 | 3 | 5 | 5 | | | 12.5 | 0 | 5 | 5 | 3.5 | 5 | 5 |
| | 25 | 0 | 3.5 | 5 | 2 | 4.5 | 5 | | 204 | 100 | 0 | 5 | 5 | 5 | 5 | 5 |
| | 12.5 | 0 | 3.5 | 5 | 2.5 | 3 | 5 | | | 50 | 0 | 5 | 5 | 5 | 5 | 5 |
| 184 | 100 | 1 | 5 | 5 | 5 | 5 | 5 | | | 25 | 0 | 5 | 5 | 5 | 5 | 5 |
| | 50 | 0 | 5 | 5 | 5 | 5 | 5 | | | 12.5 | 0 | 4.5 | 5 | 2 | 5 | 4.5 |
| | 25 | 0 | 5 | 5 | 4 | 5 | 5 | | 205 | 100 | 0 | 5 | 5 | 5 | 5 | 5 |
| | 12.5 | 0 | 5 | 5 | 4 | 5 | 5 | | | 50 | 0 | 5 | 5 | 5 | 5 | 5 |
| 185 | 100 | 0 | 5 | 5 | 5 | 5 | 5 | | | 25 | 0 | 5 | 5 | 4.5 | 5 | 5 |
| | 50 | 0 | 5 | 5 | 5 | 5 | 5 | | | 12.5 | 0 | 4.5 | 5 | 3 | 5 | 5 |
| | 25 | 0 | 5 | 5 | 4.5 | 4.5 | 5 | | 206 | 100 | 0 | 5 | 5 | 5 | 5 | 5 |
| | 12.5 | 0 | 5 | 5 | 3 | 5 | 5 | | | 50 | 0 | 5 | 5 | 5 | 5 | 5 |
| 186 | 100 | 0 | 5 | 5 | 5 | 5 | 5 | | | 25 | 0 | 5 | 4.5 | 5 | 5 | 5 |
| | 50 | 0 | 5 | 5 | 5 | 5 | 5 | | | 12.5 | 0 | 4 | 5 | 3.5 | 5 | 5 |
| | 25 | 0 | 5 | 5 | 5 | 5 | 5 | | 207 | 100 | 0 | 5 | 5 | 5 | 5 | 5 |
| | 12.5 | 0 | 4.5 | 5 | 1.5 | 4.5 | 5 | | | 50 | 0 | 5 | 5 | 5 | 5 | 5 |
| 187 | 100 | 0 | 5 | 5 | 5 | 5 | 5 | | | 25 | 0 | 5 | 5 | 3.5 | 5 | 5 |
| | 50 | 0 | 5 | 5 | 4 | 5 | 5 | | | 12.5 | 0 | 4 | 5 | 4.5 | 4.5 | 5 |
| | 25 | 0 | 4.5 | 5 | 4 | 4.5 | 5 | | 208 | 100 | 0 | 5 | 5 | 5 | 5 | 5 |
| | 12.5 | 0 | 4.5 | 5 | 2 | 3 | 5 | | | 50 | 0 | 5 | 5 | 5 | 5 | 5 |
| 188 | 100 | 0 | 5 | 5 | 5 | 5 | 5 | | | 25 | 0 | 5 | 5 | 4.5 | 5 | 5 |

TABLE 4-continued

| | | | | | | | |
|---|---|---|---|---|---|---|---|
| | 12.5 | 0 | 5 | 3.5 | 2.5 | 5 | 4.5 |
| 209 | 100 | 1 | 5 | 5 | 5 | 5 | 5 |
| | 50 | 0 | 5 | 5 | 5 | 5 | 5 |
| | 25 | 0 | 4.5 | 5 | 5 | 5 | 5 |
| | 12.5 | 0 | 5 | 5 | 5 | 5 | 5 |
| 210 | 100 | 0 | 5 | 5 | 5 | 5 | 5 |
| | 50 | 0 | 5 | 5 | 5 | 5 | 5 |
| | 25 | 0 | 5 | 5 | 4 | 5 | 5 |
| | 12.5 | 0 | 4 | 5 | 4 | 4.5 | 5 |
| 211 | 100 | 0 | 5 | 5 | 5 | 5 | 5 |
| | 50 | 0 | 5 | 5 | 5 | 5 | 5 |
| | 25 | 0 | 5 | 5 | 5 | 5 | 4.5 |
| | 12.5 | 0 | 4.5 | 5 | 4 | 5 | 5 |
| 212 | 100 | 0 | 5 | 5 | 5 | 5 | 5 |
| | 50 | 0 | 5 | 5 | 5 | 5 | 5 |
| | 25 | 0 | 5 | 5 | 4 | 5 | 5 |
| | 12.5 | 0 | 4 | 5 | 3.5 | 4.5 | 5 |
| Agent B | 100 | 5 | 5 | 5 | 2 | 4 | 4 |
| | 50 | 5 | 5 | 5 | 0 | 4 | 1 |
| | 25 | 4 | 3 | 4 | 0 | 2 | 0 |
| | 12.5 | 3 | 1 | 2 | 0 | 0 | 0 |
| Agent C | 100 | 5 | 5 | 5 | 3 | 5 | 5 |
| | 50 | 5 | 5 | 5 | 3 | 5 | 5 |
| | 25 | 5 | 5 | 5 | 2 | 5 | 5 |
| | 12.5 | 4 | 4 | 5 | 0 | 5 | 4 |
| non treatment | 0 | 0 | 0 | 0 | 0 | 0 | 0 |

Experimental Example 4

Application Test on Upland Soil

Upland alluvial clay loam was charged into each of resin vats with an area of 1/2500 are and applied with a fertilizer, after which crop seeds of soybean and cotton were sowed and then covered with the soil in a thickness of 2 to 3 cm. On the soil surface were uniformly applied the mixture of soil and seeds of weeds, i.e. large crabgrass and hat sedge. The wettable powders containing the compounds of the invention indicated in Table below obtained in Preparation Example 1 or the known agents were diluted with water and uniformly sprayed by means of a small-size powered pressed sprayer in such a manner that each effective component was applied in amounts of 50, 25 and 12.5 g per are. At the 28th day after the chemical treatment, the herbicidal effect and the phytotoxicity of the respective crops were checked. The results are shown in Table 5.

The herbicidal activity was evaluated in the same manner as in Experimental Example 1 and the phytotoxicity was evaluated in the same manner as in Experimental Example 2.

TABLE 5

| Compound No. | Dose g/a | Herbicidal effect D.S. | Herbicidal effect C.M. | Phytotoxicity Soy bean | Phytotoxicity Cotton |
|---|---|---|---|---|---|
| 5 | 50 | 5 | 5 | 0 | 0 |
| | 25 | 5 | 5 | 0 | 0 |
| | 12.5 | 3 | 5 | 0 | 0 |
| 6 | 50 | 5 | 5 | 0 | 0 |
| | 25 | 5 | 5 | 0 | 0 |
| | 12.5 | 4 | 5 | 0 | 0 |
| 7 | 50 | 5 | 5 | 0 | 0 |
| | 25 | 5 | 5 | 0 | 0 |
| | 12.5 | 5 | 5 | 0 | 0 |
| 8 | 50 | 5 | 5 | 0 | 0 |
| | 25 | 5 | 5 | 0 | 0 |
| | 12.5 | 4 | 5 | 0 | 0 |
| 9 | 50 | 5 | 5 | 0 | 0 |
| | 25 | 5 | 5 | 0 | 0 |
| | 12.5 | 5 | 5 | 0 | 0 |
| 10 | 50 | 5 | 5 | 0 | 0 |
| | 25 | 5 | 5 | 0 | 0 |
| | 12.5 | 4 | 5 | 0 | 0 |
| 11 | 50 | 5 | 5 | 0 | 0 |
| | 25 | 4 | 5 | 0 | 0 |
| | 12.5 | 4 | 5 | 0 | 0 |
| 12 | 50 | 5 | 5 | 0 | 0 |
| | 25 | 5 | 5 | 0 | 0 |
| | 12.5 | 4 | 5 | 0 | 0 |
| 13 | 50 | 5 | 5 | 0 | 0 |
| | 25 | 5 | 5 | 0 | 0 |
| | 12.5 | 5 | 5 | 0 | 0 |
| 14 | 50 | 5 | 5 | 0 | 0 |
| | 25 | 5 | 5 | 0 | 0 |
| | 12.5 | 5 | 5 | 0 | 0 |
| 15 | 50 | 5 | 5 | 0 | 0 |
| | 25 | 5 | 5 | 0 | 0 |
| | 12.5 | 5 | 5 | 0 | 0 |
| 16 | 50 | 5 | 5 | 0 | 0 |
| | 25 | 5 | 5 | 0 | 0 |
| | 12.5 | 5 | 5 | 0 | 0 |
| 17 | 50 | 5 | 5 | 0 | 0 |
| | 25 | 4 | 5 | 0 | 0 |
| | 12.5 | 4 | 5 | 0 | 0 |
| 18 | 50 | 4 | 5 | 0 | 0 |
| | 25 | 4 | 5 | 0 | 0 |
| | 12.5 | 3 | 4 | 0 | 0 |
| 35 | 50 | 5 | 5 | 0 | 0 |
| | 25 | 5 | 5 | 0 | 0 |
| | 12.5 | 4 | 5 | 0 | 0 |
| 36 | 50 | 5 | 5 | 0 | 0 |
| | 25 | 5 | 5 | 0 | 0 |
| | 12.5 | 5 | 5 | 0 | 0 |
| 37 | 50 | 5 | 5 | 0 | 0 |
| | 25 | 5 | 5 | 0 | 0 |
| | 12.5 | 5 | 5 | 0 | 0 |
| 38 | 50 | 5 | 5 | 0 | 0 |
| | 25 | 5 | 5 | 0 | 0 |
| | 12.5 | 5 | 5 | 0 | 0 |
| 39 | 50 | 5 | 5 | 0 | 0 |
| | 25 | 5 | 5 | 0 | 0 |
| | 12.5 | 4 | 5 | 0 | 0 |
| 40 | 50 | 5 | 5 | 0 | 0 |
| | 25 | 5 | 5 | 0 | 0 |
| | 12.5 | 3 | 5 | 0 | 0 |
| 41 | 50 | 5 | 5 | 0 | 0 |
| | 25 | 5 | 5 | 0 | 0 |
| | 12.5 | 3 | 5 | 0 | 0 |
| 42 | 50 | 5 | 5 | 0 | 0 |
| | 25 | 4 | 5 | 0 | 0 |
| | 12.5 | 4 | 4 | 0 | 0 |
| 43 | 50 | 5 | 5 | 0 | 0 |
| | 25 | 4 | 5 | 0 | 0 |
| | 12.5 | 4 | 5 | 0 | 0 |
| 44 | 50 | 4 | 5 | 0 | 0 |
| | 25 | 4 | 5 | 0 | 0 |
| | 12.5 | 3 | 4 | 0 | 0 |
| 45 | 50 | 4 | 5 | 0 | 0 |
| | 25 | 4 | 4 | 0 | 0 |
| | 12.5 | 2 | 4 | 0 | 0 |
| 51 | 50 | 5 | 5 | 0 | 0 |
| | 25 | 5 | 5 | 0 | 0 |
| | 12.5 | 4 | 5 | 0 | 0 |
| 52 | 50 | 5 | 5 | 0 | 0 |
| | 25 | 5 | 5 | 0 | 0 |
| | 12.5 | 5 | 5 | 0 | 0 |
| 53 | 50 | 5 | 5 | 0 | 0 |
| | 25 | 5 | 5 | 0 | 0 |
| | 12.5 | 4 | 4 | 0 | 0 |
| 54 | 50 | 5 | 5 | 0 | 0 |
| | 25 | 4 | 5 | 0 | 0 |
| | 12.5 | 4 | 4 | 0 | 0 |
| 55 | 50 | 5 | 5 | 0 | 0 |
| | 25 | 5 | 5 | 0 | 0 |
| | 12.5 | 3 | 4 | 0 | 0 |
| 56 | 50 | 4 | 5 | 0 | 0 |
| | 25 | 4 | 4 | 0 | 0 |
| | 12.5 | 3 | 4 | 0 | 0 |
| 57 | 50 | 5 | 5 | 0 | 0 |
| | 25 | 5 | 5 | 0 | 0 |
| | 12.5 | 3 | 4 | 0 | 0 |
| 58 | 50 | 5 | 5 | 0 | 0 |
| | 25 | 5 | 5 | 0 | 0 |

TABLE 5-continued

| Compound No. | Dose g/a | Herbicidal effect D.S. | Herbicidal effect C.M. | Phytotoxicity Soy bean | Phytotoxicity Cotton |
|---|---|---|---|---|---|
| | 12.5 | 3 | 5 | 0 | 0 |
| 59 | 50 | 5 | 5 | 0 | 0 |
| | 25 | 4 | 5 | 0 | 0 |
| | 12.5 | 3 | 4 | 0 | 0 |
| 61 | 50 | 4 | 5 | 0 | 0 |
| | 25 | 4 | 4 | 0 | 0 |
| | 12.5 | 3 | 4 | 0 | 0 |
| 90 | 50 | 5 | 5 | 0 | 0 |
| | 25 | 4 | 5 | 0 | 0 |
| | 12.5 | 4 | 5 | 0 | 0 |
| 91 | 50 | 5 | 5 | 0 | 0 |
| | 25 | 5 | 5 | 0 | 0 |
| | 12.5 | 4 | 4 | 0 | 0 |
| 92 | 50 | 5 | 5 | 0 | 0 |
| | 25 | 4 | 5 | 0 | 0 |
| | 12.5 | 4 | 5 | 0 | 0 |
| 93 | 50 | 5 | 5 | 0 | 0 |
| | 25 | 5 | 5 | 0 | 0 |
| | 12.5 | 3 | 5 | 0 | 0 |
| 94 | 50 | 5 | 5 | 0 | 0 |
| | 25 | 4 | 5 | 0 | 0 |
| | 12.5 | 3 | 4 | 0 | 0 |
| 95 | 50 | 5 | 5 | 0 | 0 |
| | 25 | 5 | 5 | 0 | 0 |
| | 12.5 | 3 | 4 | 0 | 0 |
| 96 | 50 | 5 | 5 | 0 | 0 |
| | 25 | 4 | 5 | 0 | 0 |
| | 12.5 | 4 | 4 | 0 | 0 |
| 97 | 50 | 4 | 5 | 0 | 0 |
| | 25 | 4 | 4 | 0 | 0 |
| | 12.5 | 3 | 4 | 0 | 0 |
| 98 | 50 | 4 | 5 | 0 | 0 |
| | 25 | 4 | 4 | 0 | 0 |
| | 12.5 | 2 | 3 | 0 | 0 |
| 99 | 50 | 5 | 5 | 0 | 0 |
| | 25 | 4 | 5 | 0 | 0 |
| | 12.5 | 4 | 4 | 0 | 0 |
| 100 | 50 | 5 | 5 | 0 | 0 |
| | 25 | 4 | 5 | 0 | 0 |
| | 12.5 | 3 | 3 | 0 | 0 |
| 101 | 50 | 4 | 5 | 0 | 0 |
| | 25 | 4 | 4 | 0 | 0 |
| | 12.5 | 2 | 3 | 0 | 0 |
| Agent A | 50 | 0 | 2 | 0 | 0 |
| | 25 | 0 | 0 | 0 | 0 |
| | 12.5 | 0 | 0 | 0 | 0 |
| Agent B | 50 | 1 | 4 | 0 | 0 |
| | 25 | 0 | 2 | 0 | 0 |
| | 12.5 | 0 | 0 | 0 | 0 |
| Agent D | 50 | 5 | 5 | 4 | 4 |
| | 25 | 5 | 5 | 2 | 3 |
| | 12.5 | 5 | 5 | 0 | 1 |
| non treatment | — | 0 | 0 | 0 | 0 |

What we claimed is:

1. An N-(2,3-epoxypropylene)-N-aralkylsulfonamide of formula (I):

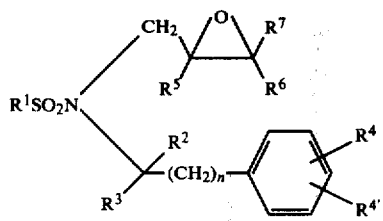

wherein
R¹ is an alkyl group, a haloalkyl group, an aralkyl group or an aryl group which may be substituted,
R² and R³, independently of each other, are a hydrogen atom or an alkyl group,
R⁴ and R⁴′, independently of each other, are a hydrogen atom, an alkyl group, an alkoxy group or a halogen atom,
R⁵, R⁶ and R⁷, independently of each other, are a hydrogen atom, an alkyl group, a haloalkyl group or an aryl group, and n is 0 or 1.

2. The compound of claim 1, wherein
R¹ is an alkyl group containing from 1 to 4 carbon atoms, a haloalkyl group containing from 1 to 4 carbon atoms, an aralkyl group, a 5,6,7,8-tetrahydro-2-naphthyl group, a 2-indanyl group or a

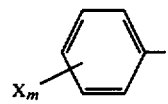

group, wherein
X is an alkyl group, a halogen atom, an alkoxy group, a nitro group, an alkylcarbonyl group, a hydroxy group, an alkenyloxy group, an epoxyalkoxy group, an aralkyloxy group; a phenoxy group, a benzyl group or a pyridyloxy group which may be substituted by an alkyl group, a halogen atom or a nitro group, a haloalkoxy group, an alkoxyalkoxy group, an alkoxycarbonyloxy group, an alkylcarbamoyloxy group, an alkoxycarbonylalkoxy group, a N-alkyl-N-phenylcarbamoyloxy group, an alkylsulfamoyloxy, group, an alkylsulfonyloxy group, a benzoyloxy group, an amino group, an alkylcarbonyloxy group, an alkoxycarbonylamino group, a di-substituted carbamoylamino group, an alkoxycarbonylalkylamino group, a cycloalkyl group or an alkylcarbamoyl group;
m is an integer of from 0 to 5,
X is the same or different when m is more than 2;
R² and R³, independently of each other, are a hydrogen atom or an alkyl group containing from 1 to 5 carbon atoms,
and R⁴ and R⁴′ independently of each other, are a hydrogen atom, a halogen atom, an alkyl group containing from 1 to 3 carbon atoms or an alkoxy group containing from 1 to 3 carbon atoms.

3. The compound of claim 2, wherein
R¹ is a 5,6,7,8-tetrahydro-2-naphthyl group, a 2-indanyl group

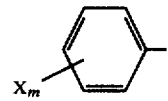

group,
wherein X is an alkyl group containing from 1 to 5 carbon atoms, a halogen atoms, an alkoxy group, a hydroxy group, an alkenyloxy group, an epoxyalkoxy group, an aralkoxy group; a phenoxy group, a benzyl group or a pyridyloxy group which group may be substituted by an alkyl group, a halogen atom or a nitro group, a haloalkoxy group, an alkoxyalkoxy group, an alkoxycarbonyloxy group, an alkylcarbamoyloxy group, an alkoxycarbonylalkoxy group, a N-alkyl-N-phenylcarbamoyloxy group, an alkylsulfamoyloxy group, an alkylsulfonyloxy group, a benzoyloxy group, an amino group, an alkylcarbonyloxy group, an alkoxycarbonylamino group, a di-substituted carbamoylamino group, an alkoxycarbonylalkylamino group, a cycloalkyl group or an alkylcarbamoyl group.

4. The compound of claim 3, wherein $R^5$, $R^6$ and $R^7$ are each a hydrogen atom, and n is 0.

5. The compound of claim 4, wherein at least one of $R^2$ and $R^3$ is an alkyl group containing from 1 to 3 carbon atoms, and $R^4$ and $R^{4'}$, independently of each other are a hydrogen atom, an alkyl group containing from 1 to 3 carbon atoms or an alkoxy group containing from 1 to 3 carbon atoms.

6. The compound of claim 5, wherein at least one of $R^2$ and $R^3$ is a methyl group.

7. The compound of claim 6, wherein
$R^1$ is a 5,6,7,8-tetrahydro-2-naphthyl group or a

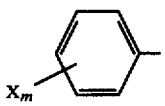

group,
wherein X is an alkyl group, m is an integer of from 0 to 4,
and $R^3$, $R^4$ and $R^{4'}$ are each a hydrogen atom.

8. The compound of claim 6, wherein X is an alkyl group or an alkoxy group, m is 0 or 1, $R^4$ is a methoxy group located at the 3-position of the benzene ring to which it is bonded, and $R^3$ and $R^{4'}$ are each a hydrogen atom.

9. The compound of claim 6, wherein X is an alkyl group, m is an integer of from 0 to 2, one of $R^2$ and $R^3$ is a methyl group and the other is an alkyl group, and $R^4$ and $R^{4'}$ are each a hydrogen atom.

10. The compound of claim 6, wherein X is a dialkylcarbamoyl group or a dialkylcarbamoyloxy group wherein the alkyl groups have 1 or 2 carbon atoms, $R^2$ is a methyl group, and $R^3$, $R^4$ and $R^{4'}$ are each a hydrogen atom.

11. A herbicidal composition, which comprises: the N-(2,3-epoxypropylene)-N-aralkylsulfonamide of claim 1 as an active ingredient and an inert carrier.

12. The herbicidal composition according to claim 11, wherein said active ingredient is the N-(2,3-epoxypropylene)-N-aralkylsulfonamide of claim 2.

13. The herbicidal composition according to claim 11, wherein said active ingredient is the N-(2,3-epoxypropylene)-N-aralkylsulfonamide of claim 3.

14. A herbicidal composition according to claim 11, wherein said active ingredient is the N-(2,3-epoxypropylene)-N-aralkylsulfonamide of claim 4.

15. The herbicidal composition according to claim 11, wherein said active ingredient is the N-(2,3-epoxypropylene)-N-aralkylsulfonamide of claim 5.

16. The herbicidal composition according to claim 11, wherein said active ingredient is the N-(2,3-epoxypropylene)-N-aralkylsulfonamide of claim 6.

17. The herbicidal composition according to claim 11, wherein said active ingredient is the N-(2,3-epoxypropylene)-N-aralkylsulfonamide of claim 7.

18. The herbicidal composition according to claim 11, wherein said active ingredient is the N-(2,3-epoxypropylene)-N-aralkylsulfonamide of claim 8.

19. The herbicidal composition according to claim 11, wherein said active ingredient is the N-(2,3-epoxypropylene)-N-aralkylsulfonamide of claim 9.

20. The herbicidal composition according to claim 11, wherein said active ingredient is the N-(2,3-epoxypropylene)-N-aralkylsulfonamide of claim 10.

* * * * *